United States Patent
Kashima et al.

(10) Patent No.: US 6,184,535 B1
(45) Date of Patent: Feb. 6, 2001

(54) METHOD OF MICROSCOPIC OBSERVATION

(75) Inventors: Shingo Kashima, Sagamihara; Yoshinori Iketaki, Ome, both of (JP)

(73) Assignee: Olympus Optical Co., Ltd., Tokyo (JP)

(*) Notice: Under 35 U.S.C. 154(b), the term of this patent shall be extended for 0 days.

(21) Appl. No.: 09/156,775

(22) Filed: Sep. 18, 1998

(30) Foreign Application Priority Data

Sep. 19, 1997 (JP) .................................................. 9-255444

(51) Int. Cl.$^7$ .................................................. G01N 21/64
(52) U.S. Cl. ..................................... 250/459.1; 250/458.1
(58) Field of Search .............................. 250/459.1, 458.1

(56) References Cited

U.S. PATENT DOCUMENTS

| | | | |
|---|---|---|---|
| 5,866,911 | 2/1999 | Baer | 250/458.1 |
| 5,952,668 | 9/1999 | Baer | 250/492.1 |

FOREIGN PATENT DOCUMENTS

| | | |
|---|---|---|
| 43 31 570 C2 | 3/1995 | (DE) . |
| 8-248200 | 9/1996 | (JP) . |
| WO 95/21393 | 8/1995 | (WO) . |

OTHER PUBLICATIONS

Konig, et al., "Cellular Response to Near–Infrared Femtosecond Laser Pulses in Two–Photon Microscopes", Optics Letters, Jan. 15, 1997, vol. 22, No. 2, pp. 135–136.

Okuzawa, et al., "Direct Observation of Second Excited $^{1,3}$(n, π*) States of Pyrazine by UV–IR Double Resonance Dip Spectroscopy", Chemical Physical Letters, Aug. 10, 1990 vol. 171, No. 4, pp. 341–346.

Kandori et al, "Picosecond Transient Absorption of Aqueous Tryptophan", J. Phys. Chem. Sep. 1993, vol. 97, No. 38 pp. 9664–9667 + Cover Page, and 3 page Table of Contents.

Primary Examiner—Constantine Hannaher
Assistant Examiner—Otilia Gabor
(74) Attorney, Agent, or Firm—Pillsbury Madison & Sutro LLP

(57) ABSTRACT

In a method of observing a specimen through a fluorescence microscope, molecules that could cause double-resonance absorption process in an appropriate manner are used to dye the specimen, and the specimen is irradiated with a plurality of light beams of different wavelengths in a good timing, so that a microscopic image with high spatial resolution is obtained.

In the microscope to be used in the method of observation, the specimen is irradiated with two light beams of different wavelength bands via an aperture with an annular-zonal structure and an optical system that has different in-focus positions for these two wavelength bands, so that one of the two light beam is focused on a surface of the specimen and the other light beam is defocused thereon. Consequently, the microscope achieves improvement of the spatial resolution as to overcome the diffraction limit determined by the wavelengths in use.

14 Claims, 15 Drawing Sheets

METHOD OF MICROSCOPIC OBSERVATION

BACKGROUND OF THE INVENTION a) Field of the Invention

The present invention relates to a method of observation in optical microscopy, specifically to that using a scanning fluorescence microscope, which achieves high spatial resolution to obtain an image with good quality by illuminating a dyed specimen with a plurality of light beams of different wavelengths.

b) Description of Related Art

Optical microscopes have a substantial history, in which various types of apparatuses have been developed and improved. On the other hand, progress in the background technology such as laser technology and electronic image technology in recent years has contributed to development of microscopes of nowadays with higher performance. In this situation, Japanese Patent Preliminary Publication No. Hei 8-248200, for example, proposes a high-performance microscope that makes it possible not only to control contrast of the image obtained but also to perform chemical analysis of the specimen. This type of microscope is explained below in spectroscopic terms.

FIG. 11 shows the electronic structure of valence electron orbits of a molecule contained in a specimen. According to the microscope disclosed by the above-mentioned Hei 8-248200, the double-resonance absorption process is used for observation of those absorption and fluorescence with respect to a selected molecule which result from specific optical transitions. The principle of the double resonance absorption process is explained below in reference to FIGS. 12–14.

First, electrons in valence electron orbits of a molecule in the ground state (hereinafter referred to as $S_0$ state) shown in FIG. 11 are excited by light waves of a certain wavelength ($\lambda_1$) to enter into the first-level excited state (hereinafter referred to as $S_1$ state), as shown in FIG. 12. Second, the electrons are excited by light waves of a different wavelength ($\lambda_2$) in a similar manner as shown in FIG. 13 to enter into the second-level excited state (hereinafter referred to as $S_2$ state). The molecule in $S_2$ state then emits fluorescence or phosphorescence to return to $S_0$ state as shown in FIG. 14.

According to the method of microscopic observation where the double-resonance absorption process is utilized, the absorption process shown in FIGS. 12 and 13 and emission of fluorescence or phosphorescence shown in FIG. 14 are used for observation of an absorption image and a luminescence image.

In such a method, first, molecules in a specimen are excited by a resonance wavelength $\lambda_1$ of laser light or the like to enter into $S_1$ state shown in FIG. 12. The number of $S_1$-state molecules per unit volume (population) increases as the intensity of the light with which the specimen is irradiated increases. A linear absorption coefficient is given as the product of {absorption cross section per molecule} and {number of molecules per unit volume}. Therefore, in the molecular excited state shown in FIG. 13, the linear absorption coefficient for the light of resonance wavelength $\lambda_2$, with which the molecules are irradiated in succession to the irradiation with the light of wavelength $\lambda_1$, depends on the intensity of the light of the wavelength $\lambda_1$. Accordingly, the linear absorption coefficient for the light of the wavelength $\lambda_2$ is controllable by the intensity of the light of the wavelength $\lambda_1$. With respect to a transmission image of the specimen formed with transmitted light of the wavelength $\lambda_2$, it means that the contrast of the transmission image is fully controllable with amount of light of the wavelength $\lambda_1$.

On the other hand, if decay from $S_2$ state could occur as being accompanied by emission of fluorescence or phosphorescence as shown in FIG. 14, the luminous intensity is proportionally related with the number of $S_1$-state molecules. Accordingly, where the microscope is used as a fluorescence microscope, also, control of image contrast is possible. In addition, chemical analysis of the specimen also is possible in such application of the microscope.

The outermost shells, or valence electron orbits, which are shown in FIG. 11, possess energy levels peculiar to each molecule. Therefore, fluorescence caused by irradiation with light of wavelength $\lambda_1$ varies with molecules irradiated. Similarly, when irradiated with the light of the wavelength $\lambda_2$, a molecule emits fluorescence peculiar to it. If a specimen is irradiated with light of a single wavelength, as conventionally done, absorption image or fluorescence image of a certain molecule is observable to some degree. However, the chemical composition of the specimen cannot be accurately identified, because, in general, the wavelength ranges of the absorption bands of several molecules overlap one another.

In contrast, according to the method of microscopic observation utilizing the double-resonance absorption process, molecules to absorb or emit light are limited by two wavelengths $\lambda_1$ and $\lambda_2$, and thus accurate identification of chemical composition of the specimen is possible. Furthermore, when a valence electron is excited, light having a specific electric field vector in reference to a molecular axis is strongly absorbed. Therefore, if the absorption image or the fluorescence image is photographed upon directions of polarization of light waves of wavelengths $\lambda_1$ and $\lambda_2$ being controlled, orientations of individual molecules of one kind can be identified.

Furthermore, according to some recent proposals, a fluorescence microscope is able to have such a high spatial resolution as to overcome the diffraction limit by using the double-resonance absorption process. The principle of such a microscope is described in reference to FIG. 15.

FIG. 15 schematically shows the double-resonance absorption process concerning a certain molecule. The molecule in $S_0$ state is excited by wavelength $\lambda_1$ to enter into $S_1$ state, and then is excited by wavelength $\lambda_2$ to $S_2$ state. As schematically illustrated, fluorescence from the $S_2$-state molecule is extremely weak.

A very interesting phenomenon can be expected with respect to molecules of a kind having the above-described optical property, as explained below in reference to FIG. 16. FIG. 16 introduces abscissa (direction of X) for presenting the spatial extension in the model of double-resonance absorption process similar to FIG. 15. The spatial region $A_1$ represents a region irradiated with the wavelength $\lambda_2$, while the spatial region $A_0$ represents a region that is not irradiated with the wavelength $\lambda_2$.

In the spatial region $A_0$, a multitude of molecules in $S_1$ state are generated by excitation by the light of the wavelength $\lambda_1$, when fluorescence of a wavelength $\lambda_3$ appears. In the spatial region $A_1$, however, molecules with $S_1$ state are excited to enter into $S_2$ or much higher level state almost at the moment as produced, and thus cannot survive. This phenomenon is confirmed with respect to several kinds of molecules. Therefore, in the spatial region $A_1$, fluorescence emission is thoroughly repressed, because fluorescence of wavelength $\lambda_3$ is completely extinguished and decay from $S_2$ state does not involve fluorescence. Consequently, fluorescence resides only in the spatial region $A_0$.

This result is of great importance in microscopy. According to a conventional scanning laser microscope, a specimen is scanned by a microbeam, which is formed by focusing laser light. The irradiation region with the microbeam is determined by the diffraction limit, which is determined by the numerical aperture of the focusing lens and the wavelength of the laser light. In principle, spatial resolution cannot be free from the diffraction limit. However, if the beams of wavelengths $\lambda_1$ and $\lambda_2$ spatially overlap with each other in an appropriate manner, the fluorescence region is limited by irradiation with the wavelength $\lambda_2$ as shown in FIG. 16. In this condition, the fluorescence region is narrower than the irradiation region with the wavelength $\lambda_1$, which is determined by the numerical aperture of the focusing lens and the wavelength. In other words, substantial improvement of the spatial resolution is achieved. As discussed above, application of the double-resonance absorption process can realize fluorescence microscopy that overcomes the diffraction limit (super-resolution microscopy using the double-resonance absorption process).

In fluorescence microscopy, a specimen (mainly a biological specimen) usually is dyed with special molecules called "fluorescence probe" (or "fluorescence labeler"). A fluorescence probe absorbs a specific wavelength to emit relatively intense fluorescence. Application of such a fluorescence probe to the above-mentioned microscopy utilizing the double-resonance absorption process would be considered effective. However, only a few examples of molecules such as tryptophan and adenine have been applied to fluorescence microscopy in practice to prove their effectiveness as fluorescence probe. Tryptophan and adenine exist in the form of amino acid molecules or a base of a nucleic acid contained in biological cells. They are so special molecules as to emit fluorescence themselves in the cells.

In practice, kinds of molecules that can be observed without dye are limited in number; composition of most kinds of molecules cannot be known without dye. A fluorescence probe has a favorable property that a specific kind of molecules that are the object of observation can be selectively dyed with it upon its functional group been appropriately selected. To conform to the above-mentioned super-resolution microscope using the double-resonance absorption process, and to fully exploit its performance, it is necessary to select appropriate fluorescence probe molecules that could cause the above-mentioned double-resonance absorption process in an appropriate manner, as well as to optimize irradiation timing of the specimen with two wavelengths $\lambda_1$ and $\lambda_2$. Precedent studies, however, have neither disclosed an appropriate timing of irradiation nor specified certain molecules as the fluorescence probe.

SUMMARY OF THE INVENTION

An object of the present invention is to provide a method of fluorescence microscopic observation that allows a microscopic image to be observed with high spatial resolution, by irradiating a specimen with a plurality of wavelengths in an appropriate timing, upon the specimen being dyed with molecules that could cause double-resonance absorption process in an appropriate manner.

In order to attain the above-mentioned object, the method includes a step of dying a specimen with molecules each having at least three quantum states inclusive of a ground state, and a step of observing the specimen through a microscope. The microscope comprises a light source device for emitting light of a wavelength $\lambda_1$ that excites the molecules from the ground state to a first-level excited state and light of a wavelength $\lambda_2$ that excites the molecules from the first-level excited state to a second or much higher level excited state, a focusing optical system for focusing the light of the wavelength $\lambda_1$ and the light of the wavelength $\lambda_2$ on the specimen, a photodetector for detecting luminescence which occurs according as the molecules with which the specimen is dyed decay to return to the ground state, and an irradiation overlapping means for overlapping a region irradiated with the light of the wavelength $\lambda_1$ with a region irradiated with the light of the wavelength $\lambda_2$, that a region in which the luminescence accompanying the decay of the molecules from the first-level excited state to the ground state is limited by the irradiation overlapping means, through which the specimen is irradiated with the light of the wavelength $\lambda_1$ and the light of the wavelength $\lambda_2$. The molecules with which the specimen is dyed are used as fluorescence probe molecules and have such a property that relaxation process with heat emission is predominant over relaxation process with fluorescence emission in a transition of decay from a higher-level energy state except the first-level excited state to the ground state.

In addition, according to the method of the present invention, the polarization conditions of the light of the wavelength $\lambda_1$ and the light of the wavelength $\lambda_2$ are controlled independent of or correlative to each other.

In addition, according to the method of the present invention, time duration of irradiation with the wavelength $\lambda_1$ and the wavelength $\lambda_2$ is shorter than a fluorescence lifetime of the molecules with which the specimen is dyed, specifically, one-tenth of the lifetime.

In addition, the molecules with which the specimen is dyed has a fluorescence lifetime longer than 1 nsec.

In addition, each of the molecules with which the specimen is dyed forms a double bond, specifically containing at least one six-membered ring as a chemical base.

In addition, the dyed specimen is observed in a solution of pH 6–11.5.

In addition, according to the method of the present invention, detection of fluorescence is performed after irradiation with the light of the wavelength $\lambda_1$ and the light of the wavelength $\lambda_2$ is completed.

In addition, irradiation with the light of the wavelength $\lambda_1$ is completed before irradiation with the light of the wavelength $\lambda_2$ is commenced.

Alternatively, the specimen is irradiated with the light of the wavelength $\lambda_1$ and the light of the wavelength $\lambda_2$ simultaneously.

In addition, time duration of irradiation with the light of the wavelength $\lambda_2$ is longer than that with the light of the wavelength $\lambda_1$.

This and other objects as well as features and advantages of the present invention will become apparent from the following detailed description of the preferred embodiments when taken in conjunction with the accompanying drawings.

DETAILED DESCRIPTION OF THE PREFERRED EMBODIMENTS

Figure 1:
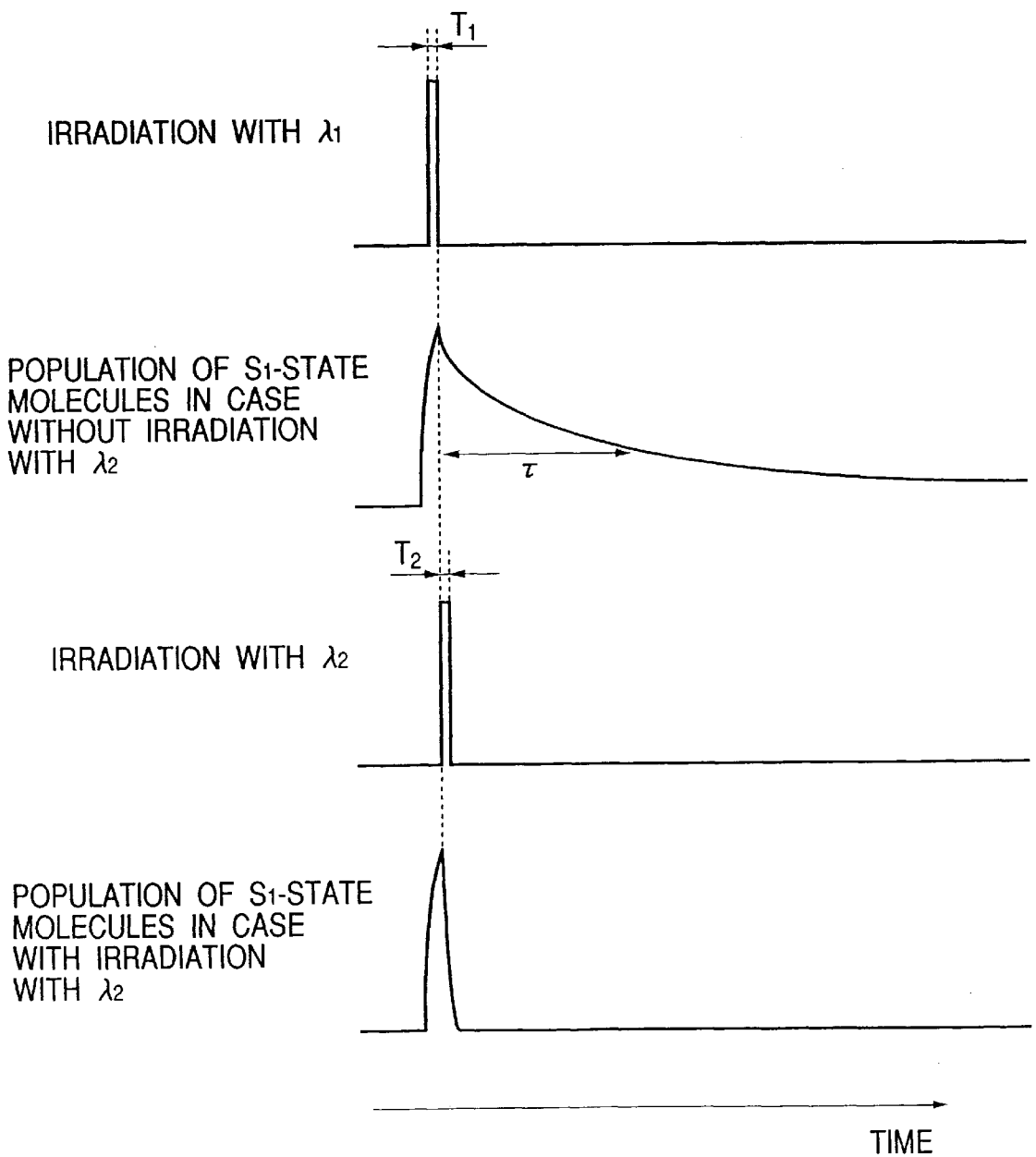
FIG. 1 is a time chart for showing a population of molecules that are excited to $S_1$ state, where the specimen is irradiated with light of a wavelength $\lambda_1$ for a time duration $T_1$, until irradiation with light of a wavelength $\lambda_2$ for a time duration $T_2$ is commenced.

The preferred embodiments of the present invention are described below in reference to the drawings, in which like reference symbols indicate members or concepts having like functions or meanings. First, preceding the descriptions of the individual embodiments, explanation will be made of the principle and effect of the present invention in view of quantum chemistry in reference to FIGS. 1 through 5.

The essence of the present invention exists in that a specimen is dyed with molecules each of which has at least three quantum states inclusive of the ground state and has a property that relaxation process with heat emission is predominant over relaxation process with fluorescence emission in a transition of decay from a higher-level energy state except the first-level excited state to the ground state. Use of such molecules facilitates observation via a super-resolution microscope utilizing the double-resonance absorption process. Upon being treated with a biochemical dyeing technique using such molecules, a biological specimen is irradiated with light of a wavelength $\lambda_1$, which excites the molecules from $S_0$ state to $S_1$ state, and successively is irradiated with light of a wavelength $\lambda_2$, which excites the molecules from $S_1$ state to a much higher level state, whereby fluorescence emission from the $S_1$-state molecules are repressed. According to the present invention, such optical properties of the molecules are utilized to control a spatial region of fluorescence appropriately for improving the spatial resolution.

In general, atoms composing a molecule are combined together via σ bond or π bond. The molecular orbital of a molecule includes σ orbital and π orbital. Electrons existing in these orbitals play an important role for bonding the atoms. Specifically, electrons in the a orbital firmly bond the atoms together and determine interatomic distances, or the skeletal structure of the molecule.

In contrast, electrons in the π orbital scarcely contribute to bond of atoms, but is bound to the entire molecule with a very weak force.

In many cases, if an electron in the σ orbital is excited by light, interatomic distance of the molecule is largely changed, to cause drastic change in molecular structure such as dissociation of the molecule. As a result, most of the kinetic energy of the atoms and the energy given to the molecule by the light for the structural change is transformed into heat. The energy for excitation is not consumed in the form of fluorescence, or light. Furthermore, since the structural change of the molecule takes place very quickly (within a time shorter than 1 picosecond), even if fluorescence could occur in the process of the structural change, fluorescence lifetime should be extremely short.

On the other hand, if electrons in the π orbital are excited, the molecule is kept at a high, quantum excited level for a long time with its structure being little changed, while emitting fluorescence on the order of nanoseconds to decay. According to the quantum chemistry, that a molecule has the π orbital is equivalent to that the molecule has a double bond. Therefore, the present inventors propose to choose molecules that have abundant double bonds, as the fluorescence probe molecules.

Furthermore, it is known that, among molecules having double bond, molecules that contain six-membered rings such as benzene and pyrazine behave such that fluorescence from $S_2$ state is extremely weak (M. Fujii, et al., "Direct observation of second excited $^{1,3}$ (n, π*) states of pyrazine by UV-IR double resonance dip spectroscopy", Chemical Physics Letters, Vol. 171, No. 4, Aug. 10, 1990, pp. 341–346). Therefore, if molecules containing six-membered rings such as benzene or pyrazine are used as the fluorescence probe, the double-resonance absorption process can effectively facilitate fluorescence microscopy because fluorescence lifetime from $S_1$ state is long and exciting the $S_1$-state molecules to make them enter into $S_2$ state can easily repress fluorescence. In other words, when a specimen is subject to observation upon being dyed with such fluorescence probe molecules, the fluorescence image of the specimen can be obtained with high spatial resolution. In addition, if a chemical base on a side chain of the fluorescence probe molecule is appropriately adjusted, a specific chemical tissue in the specimen is selectively dyed and thus chemical composition of the specimen can be analyzed in detail. As discussed above, according to the present invention, molecules that contain six-membered rings are preferably used as a dye.

In general, the double-resonance absorption process takes place when parameters such as wavelengths and polarization conditions of the two light waves satisfy certain conditions. Therefore, molecular structure can be known in detail. Relation between the polarization planes of two light waves and the direction of orientation of a molecule strongly affects the double-resonance absorption process. When the respective polarization planes of the light waves and the direction of orientation of the molecule form certain angles, strong absorption can be caused by the double-resonance absorption process. Therefore, if a specimen is irradiated with two wavelengths simultaneously and the polarization planes of the respective light waves are rotated, degree of fluorescence extinction changes. An observer can additionally obtain information on spatial orientations of tissues in the specimen by observing how the degree of fluorescence extinction changes. Alternatively, the observer can know the spatial orientations of the tissues by adjusting the wavelengths of two light waves without rotating the polarization planes thereof. As described above, according to the present invention, high analytic performances can be attained, in addition to the super-resolution.

According to the present invention, appropriate timing of irradiation of the specimen, in addition to the use of the fluorescence molecules that allows effective fluorescence repression, is proposed for the super-resolution microscopy using the double-resonance absorption process.

The super-resolution microscopy using the double-resonance absorption process is based on a technique in which the fluorescence probe molecules are excited by light of a wavelength $\lambda_1$ and fluorescence derived from the excitation is extinguished by further excitation by light of a wavelength $\lambda_2$. According to the present invention, a specimen that is dyed with fluorescence probe molecules is irradiated with light of a wavelength $\lambda_1$ for a time duration $T_1$ and then is irradiated with light of a wavelength $\lambda_2$ for a time duration $T_2$ in succession, wherein the time duration of irradiation with each wavelength is shorter than a time duration for which a fluorescence probe molecule emits fluorescence (i.e. the lifetime of the $S_1$-state molecule). In qualitative terms, first, the specimen is irradiated with the light of the wavelength $\lambda_1$ for a time duration $T_1$, which is considerably shorter than the lifetime of the fluorescence probe molecule in $S_1$ state, so that $S_1$-state molecules are produced in an observation region of the specimen. Immediately after that, a region of the specimen that is unnecessary for observation is irradiated with light of a wavelength $\lambda_2$ for a time duration $T_2$, which also is considerably shorter than the lifetime of the fluorescence probe molecule in $S_1$ state, so that $S_1$-state molecules are excited to the $S_2$ state in the non-observation region of the specimen for extinguishing fluorescence there. This process is explained below quantitatively.

In general, if irradiation with the wavelength $\lambda_1$ is commenced to excite $S_1$-state molecules into $S_2$ state, the process of excitation can be expressed by the following rate equation:

$$-\frac{dN}{dt} = NI_0\sigma_{01} - \frac{(N_0 - N)}{\tau} \tag{1}$$

where $N_0$ is a number of molecules with which the specimen is dyed per unit volume, $I_0$ is a photon flux of the light of the wavelength $\lambda_1$, N is a number of molecules in $S_0$ state as time t elapses since the commencement of the irradiation with the wavelength $\lambda_1$, $\tau$ is a lifetime of a molecule in $S_1$ state, and $\sigma_{01}$ is an absorption cross section of a molecule when the molecule is made to cause transition from $S_0$ state to $S_1$ state by the light of the wavelength $\lambda_1$.

If Equation (1) is solved, a number n of molecules in $S_1$ state as time t elapses after the commencement of the irradiation with the wavelength $\lambda_1$ is obtained as shown in the following equation:

$$n = \frac{N_0 I_0 \sigma_{01} \tau}{(1 + I_0 \sigma_{01} \tau)} \cdot \left[1 - e^{[-(I_0 \sigma_{01} + \frac{1}{\tau})t]}\right] \tag{2}$$

where $n = N_0 - N$

Here, if the irradiation with the wavelength $\lambda_1$ is performed to satisfy the following condition (3), Equation (2) can be rewritten as the following approximation (4).

$$\left(I_0 \sigma_{01} + \frac{1}{\tau}\right) t \cong 0 \tag{3}$$

$$n \approx I_0 \sigma_{01} N_0 t \tag{4}$$

From Expressions (3) and (4), We can know that if the time duration of irradiation with the wavelength $\lambda_1$ is shorter than the lifetime of the $S_1$-state molecule and the photon flux $I_0$ of the light of the wavelength $\lambda_1$ is small, the number n of $S_1$-state molecules per unit volume is approximately proportional to the time t since the commencement of the irradiation with the wavelength $\lambda_1$.

Here, the discussion proceeds to the condition where the irradiation with the wavelength $\lambda_1$ is made for a time duration $T_1$, until irradiation with the wavelength $\lambda_2$ is commenced to excite $S_1$-state molecules into $S_2$ state. The rate equation with respect to n can be written as follows:

$$\frac{dn}{dt} = -\sigma_{12} I_1 n - \frac{n}{\tau} \tag{5}$$

where $I_1$ is a photon flux of the light with the wavelength $\lambda_2$, n is a number of molecules per unit volume as time $(T_1+t)$ elapses since the irradiation with the wavelength $\lambda_1$, and $\sigma_{12}$ is an absorption cross section of a molecule when the molecule is made to cause transition from $S_1$ state to $S_2$ state by the light of the wavelength $\lambda_2$.

When the irradiation with the wavelength $\lambda_2$ for the time duration $T_2$ is completed after the irradiation with the wavelength $\lambda_1$ for the time duration $T_1$, we can obtain the value of n as expressed in the following equation by solving Equation (5):

$$n = (I_0 \sigma_{01} N_0 T_1) \cdot e^{-(\sigma_{12} I_1 + \frac{1}{\tau})T_2} \tag{6}$$

If it were not for the irradiation with the wavelength $\lambda_2$ at all, or $I_1=0$, Equation (6) derives the following equation:

$$n = (I_0 \sigma_{01} N_0 T_1) \cdot e^{-\frac{T_2}{\tau}} \qquad (7)$$

Equation (6) expresses the number of $S_1$-state molecules per unit volume in the region where fluorescence is repressed (fluorescence extinction region), while Equation (7) expresses the number of $S_1$-state molecules per unit volume in the region where fluorescence is not repressed (fluorescence region). The intensity $F_1$ of fluorescence emitted from the fluorescence region and the intensity $F_2$ of fluorescence emitted from the fluorescence extinction region are given by the following equations, respectively:

$$F_1 = \Phi(I_0 \sigma_{01} N_0 T_1) \cdot e^{-(\sigma_{12} I_1 + \frac{1}{\tau}) T_2} \qquad (8)$$

$$F_2 = \Phi(I_0 \sigma_{01} N_0 T_1) \cdot e^{-\frac{T_2}{\tau}} \qquad (9)$$

Equations (8) and (9) derive the fluorescence repression ratio $F_1/F_2$ as follows:

$$\frac{F_1}{F_2} = e^{-\sigma_{12} I_1 T_2} \qquad (10)$$

Where the irradiation process with two wavelengths $\lambda_1$ and $\lambda_2$ takes place in the timing shown in FIG. 1, fluorescence from the region that is not necessary for observation is repressed with the ratio obtained by Equation (10). As is known from Equation (10), we can repress fluorescence at a desirable ratio by appropriately adjusting $I_1$ and $T_2$ under the condition $T_2 < \tau$.

Figure 2:
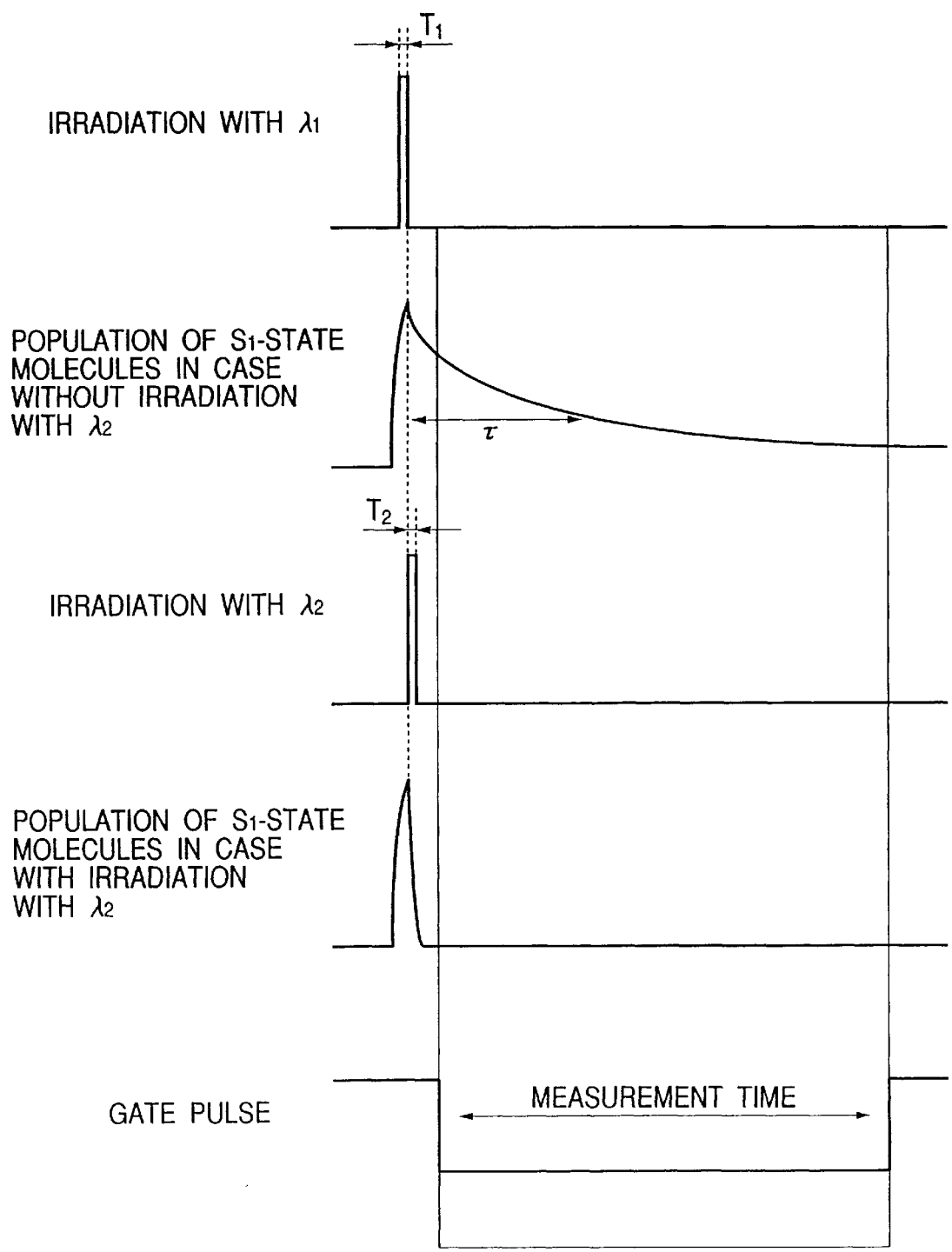
FIG. 2 is a time chart for showing a timing of measuring fluorescence emitted from the observation region of the specimen, where the specimen is irradiated with light of a wavelength $\lambda_1$ for a time duration $T_1$, until irradiation with light of a wavelength $\lambda_2$ for a time duration $T_2$ is commenced.

According to the present invention, basically, a sufficient time is taken to measure the intensity of fluorescence emitted from the observation region, after the irradiation with the wavelength $\lambda_2$ is completed, as shown in FIG. 2. This timing allows the fluorescence from the observation region to be measured with little fluorescence from the reppressed region existing on the background, i.e. in a very good S/N ratio condition.

Figure 3:
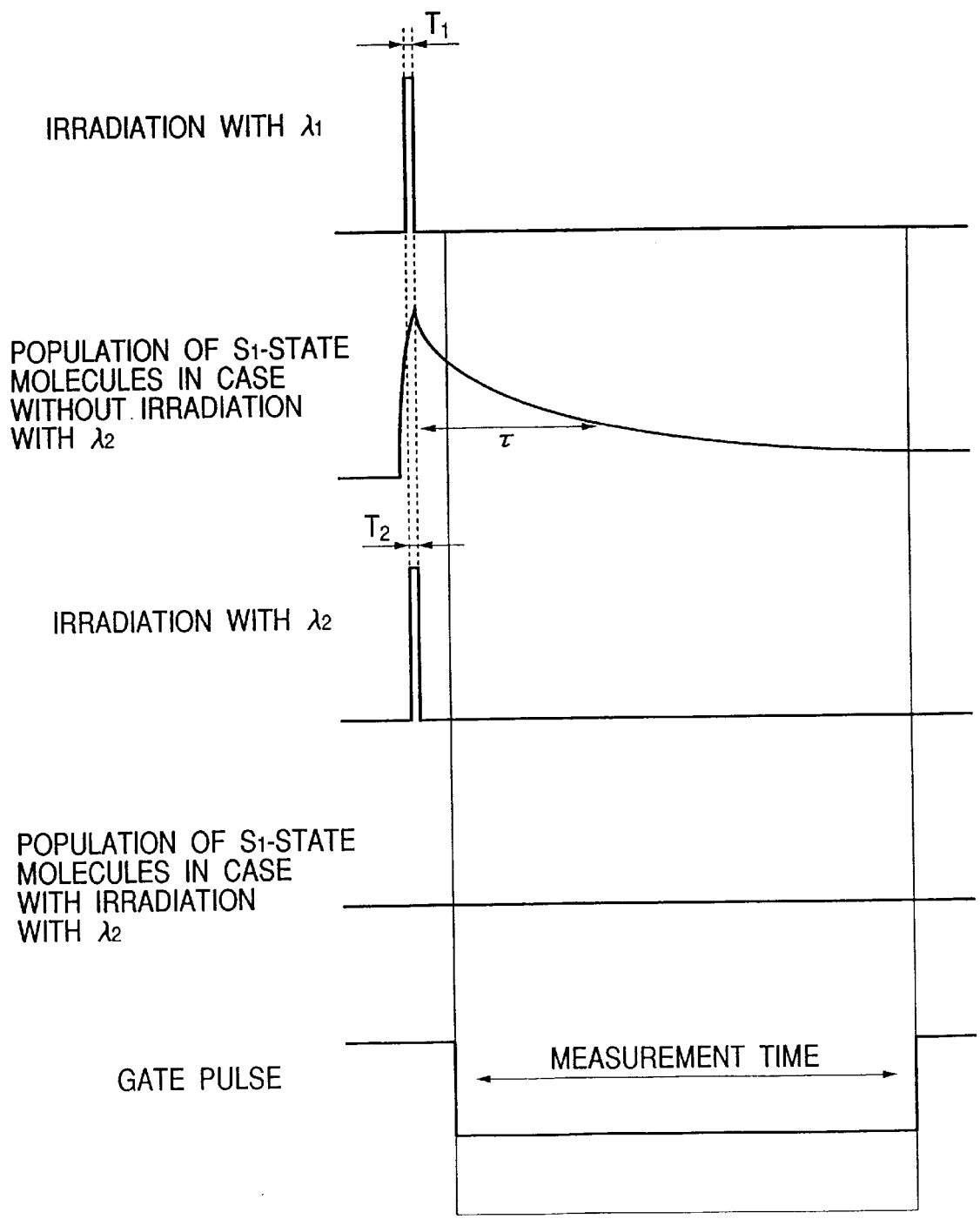
FIG. 3 is a time chart for showing a timing of measuring fluorescence emitted from the observation region of the specimen, where the specimen is irradiated with light of the wavelength $\lambda_1$ and light of the wavelength $\lambda_2$ simultaneously for a short time duration.
Figure 4:
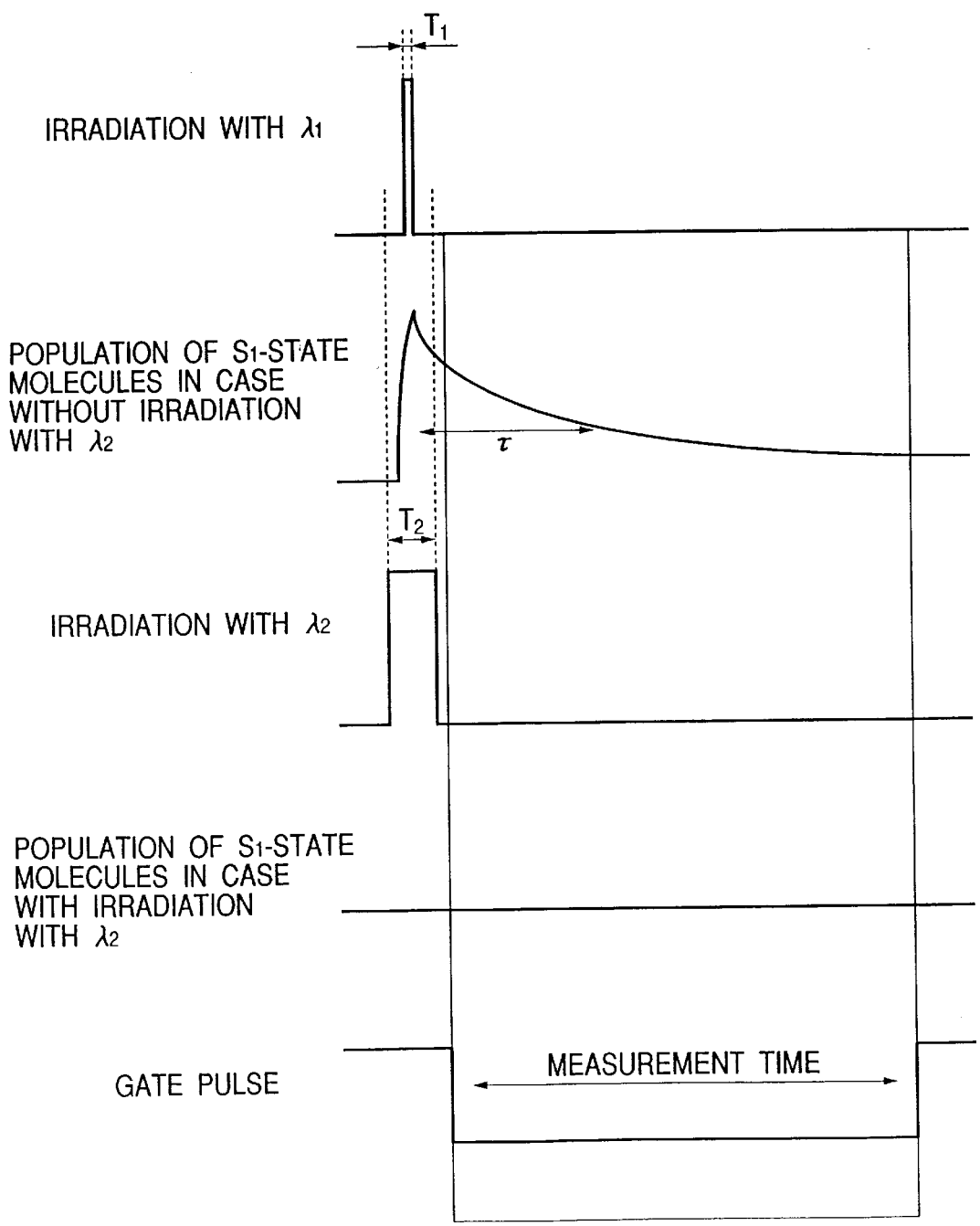
FIG. 4 is a time chart for showing a timing of measuring fluorescence emitted from the observation region of the specimen, where a time during which irradiation with a wavelength $\lambda_2$ occurs is longer than a time during which irradiation with the wavelength $\lambda_1$ occurs a the former overlaps the latter.
Figure 5:
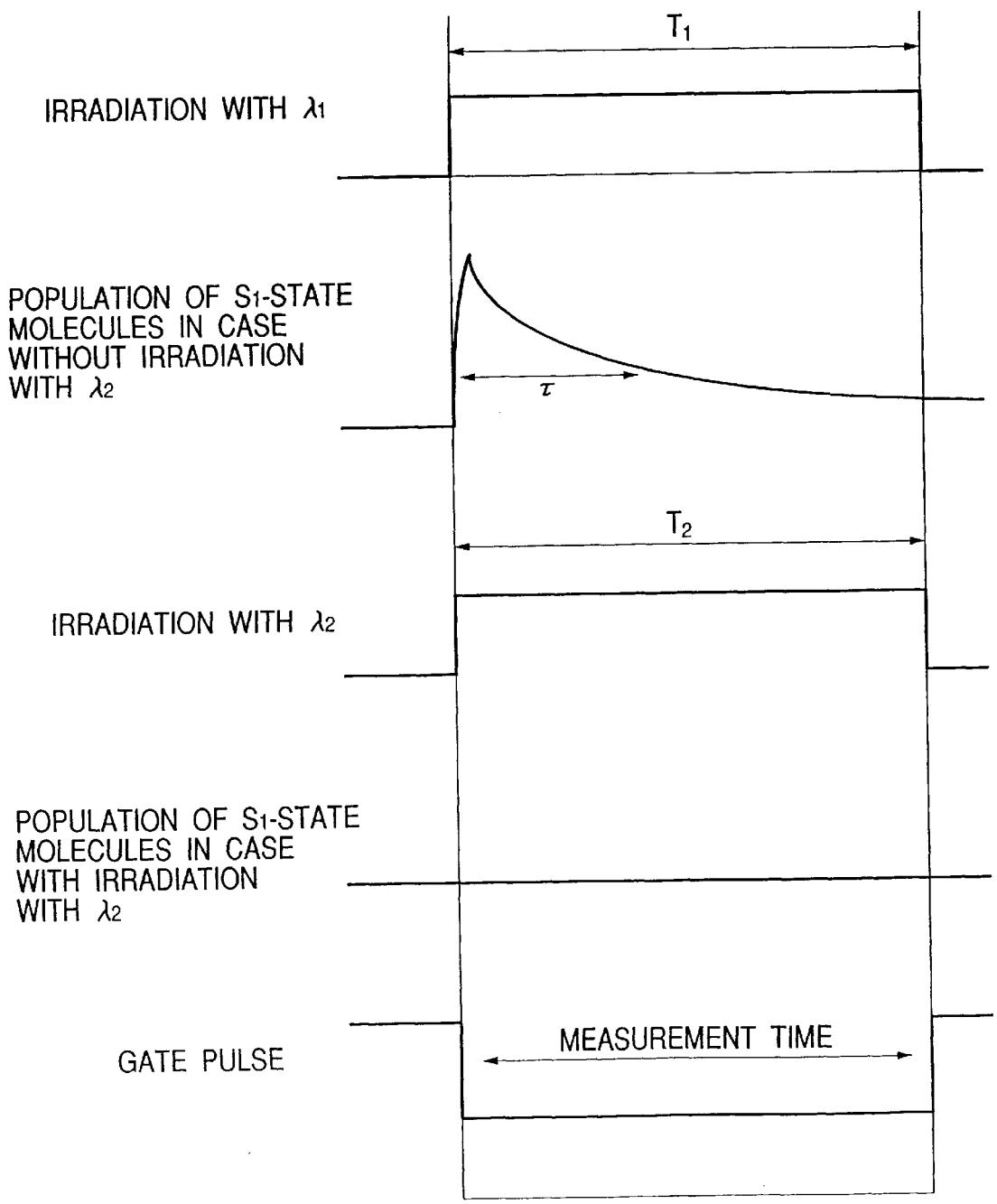
FIG. 5 is a time chart for showing a timing of measuring fluorescence emitted from the observation region of the specimen, where the specimen is irradiated with light of a wavelength $\lambda_1$ and light of a wavelength $\lambda_2$ simultaneously for a long time duration.

If the irradiation and the measurement are done in either of the timing shown in FIGS. 3 or 4, effective measurement of fluorescence can be achieved, also. It is noted that in either case of FIGS. 2, 3 or 4, the condition $T_1$, $T_2 < \tau$ should be satisfied to assure the effectiveness. If $T_1$, $T_2 > \tau$, the $S_1$-state molecules decay to return to $S_0$ state during the irradiation with the wavelengths $\lambda_1$ and $\lambda_2$ and thus fluorescence from the observation region also is extinguished. One could choose an alternative approach in which the specimen is irradiated with the light of the wavelength $\lambda_1$ and the light of the wavelength $\lambda_2$ simultaneously and the measurement also is performed during the irradiation, as shown in FIG. 5, to obviate the above-mentioned defect of the case where $T_1$, $T_2 > \tau$. According to this approach, however, the intense exciting light of the wavelengths $\lambda_1$, and $\lambda_2$ would be received by a detector during measurement. Therefore, it is preferred that the irradiation is made according to the timing shown in FIGS. 2, 3 or 4 under the condition $T_1$, $T_2 < \tau$.

According to the present invention, a detector detects the fluorescence emitted from the observation region immediately after the completion of the irradiation. Also, according to the present invention, a commercially-available, general-purpose logic circuit is employed to generate a gate signal, based on which an electric signal that is output from the detector is taken into a memory of a personal computer. As discussed above, the method of the present invention is effective if the irradiation time of the specimen is shorter than the fluorescence life of the molecules with which the specimen is dyed, as shown in the time charts of FIGS. 1–4. On the other hand, at present, switching speed of such a general-purpose logic circuit as is commercially available is about 1 nsec. Therefore, the lifetime $\tau$ is desired to be longer than 1 nsec. If the lifetime were not longer than 1 nsec, fluorescence phenomenon from the observation region should be ceased before the detector or the measurement circuit is activated ("Texas Instruments ALS/AS Advanced Bipolar Logic Family Databook", Nippon Texas Instruments, 1991).

Considering the circumstances mentioned above, the present inventors add the condition that the fluorescence probe with which the specimen is dyed has to have the fluorescence lifetime longer than 1 nsec.

The fluorescence is preferred to be weak in the fluorescence repression region, as discussed above, whereas, in view of improvement of S/N ratio, the fluorescence intensity is preferred to be high in the effective fluorescence region, from which measurement data is to be picked up. Therefore, the measurement of the fluorescence intensity is desirably performed at a moment when the number of $S_1$-state molecules is sufficiently comparable to that counted immediately after excitation with the wavelength $\lambda_1$. According to Equation (7), the number of excited molecules is exponentially decreased by a time constant determined by the lifetime of the molecules. Therefore, if time duration $T_1$, $T_2$ for irradiation is considerably short in reference to the lifetime $\tau$ of the molecules, fluorescence with sufficient intensity (i.e. a signal with effective signal strength) can be obtained from the $S_1$-state molecules for measurement, as could be done immediately after the excitation by the light of the wavelength $\lambda_1$. Especially when $T_1$ and $T_2$ are as much as one tenth of the fluorescence lifetime $\tau$ of the molecules, the number of $S_1$-state molecules at the end of the irradiation is 90% of that immediately after the excitation, and thus a sufficient signal strength is obtained from the effective fluorescence region.

First Embodiment $\epsilon$-adenosine (1, N6-ethenoadenosine) is a typical fluorescence probe. According to the method of the first embodiment, observation is made using, for example, molecules of $\epsilon$-adenosine as fluorescence probe molecules.

In many enzyme systems, $\epsilon$-adenosine proves to be a good probe for indicating the distributed amount of ATP or ADP, as acting in the form of nucleotide ($\epsilon$-ATP, $\epsilon$-ADP). On the other hand, that it has a high fluorescence yield and that its fluorescence spectrum is not overlapped with those of nucleic acids and proteins in the observing wavelength region are advantages of $\epsilon$-adenosine as applied to biological specimens. Furthermore, its fluorescence wavelength and fluorescence yield are not affected by the polarization etc. of the solvent, but shift toward the shorter-wavelength side as the viscosity of the environment increases. Therefore, if $\epsilon$-adenosine is applied to a specimen such as a protein, the wavelength of fluorescence emission can be an index of the binding degree of a nucleotide bonding site or of the viscosity of the environment.

With these advantageous properties, $\epsilon$-adenosine is available for a variety of studies; researchers can learn a structural change of an enzyme by observing a change of fluorescence spectrum, learn a structural change near the active center of actin or myosin by observing energy transfer, identify a nucleotide bonding site of a chloroplast conjugate factor by observing polarization condition and fluorescence extinction, etc.

In addition, ε-adenosine has physical properties as shown in TABLE 1. Specifically, its $S_1$ excited-state lifetime is extremely long (fluorescence lifetime of 20 nsec in an aqueous solution of pH 7.0). Therefore, if ε-adenosine is used as fluorescence probe molecules with which a biological specimen is dyed and the specimen is observed through a super-resolution microscope using the double-resonance absorption process, detail analysis of chemical composition of a nucleotide bonding site can be realized with high spatial resolution.

TABLE 1

PHYSICAL PROPERTIES OF ε-ADENOSINE

| | |
|---|---|
| Molecular Weight | 327.73 |
| Solubleness/Solvent | Water Soluble |
| Fluorescence Lifetime | 20 nsec |
| Fluorescence Yield | 0.56 |
| Maximum Absorption Wavelength | 294 nm |
| Maximum Fluorescence Wavelength | 415 nm |

Description of the first embodiment hereinafter will be made based on a case where ε-adenosine is used as the fluorescence probe molecules. According to the first embodiment, a super-resolution microscope that utilizes the double-resonance absorption process is employed. Thus, the general structure and function of such a microscope is described before explaining the specific method of the first embodiment in reference to FIGS. 6A, 6B and 7.

Figure 6A:
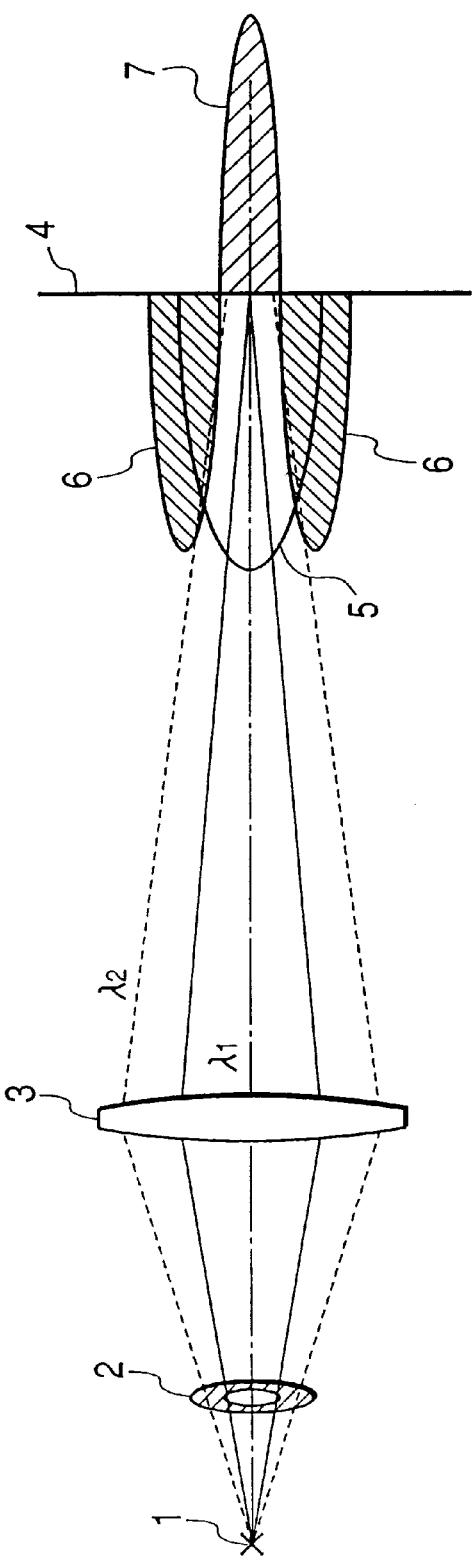
FIG. 6A shows a basic configuration of an optical system, as a main constituent, of such a super-resolution microscope utilizing the double-resonance absorption process as used in the method of the present invention, along with image patterns of the optical system.

The optical system shown in FIG. 6A, as the main constituent of the super-resolution microscope utilizing the double-resonance absorption process, produces a microbeam. In this optical system, a light source 1 is designed to emit light of discrete wavelengths $\lambda_1$ and $\lambda_2$ from the same emitting point. The light of wavelengths $\lambda_1$ and $\lambda_2$ from the light source 1 is incident on an aperture 2, which has an annular-zonal structure. The light transmitted through the aperture 2 is led to a specimen surface 4 through an optical system 3 having different focal lengths for a wavelength band that includes $\lambda_1$ and a wavelength band that includes $\lambda_2$, so that the specimen surface 4 is irradiated with light of the wavelength $\lambda_1$ focused thereon and with light of the wavelength $\lambda_2$ defocused there. The specimen is mounted on a stage (not shown), which is movable in such a manner that the specimen can be scanned two-dimensionally on an image surface of the optical system 3 and in a direction of the optical axis. To perform two-dimensional scanning with the microbeam, another configuration may be applicable, where the microbeam itself is moved using a scanning mirror or the like.

Figure 6B:
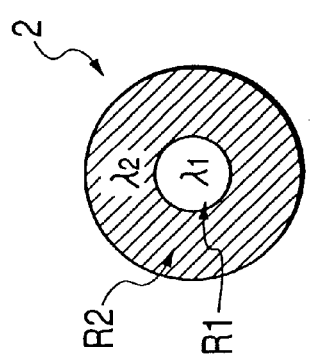
FIG. 6B is a front view of the aperture provided for the optical system shown in FIG. 6A.

The aperture 2 with the annular-zonal structure has a peculiar construction. As shown in FIG. 6B, the aperture 2 has a double annular-zonal structure composed of a region $R_1$ (central portion) and a region $R_2$ (annular-zonal portion). The region $R_1$ has a sufficiently high transmittance for the light of the wavelength $\lambda_1$ but has a very poor transmittance for the light of the wavelength $\lambda_2$. On the other hand, The region $R_2$ has a sufficiently high transmittance for the light of the wavelength $\lambda_2$ but has a very poor transmittance for the light of the wavelength $\lambda_1$.

Application of evaporation techniques would facilitate manufacture of the aperture 2 with the above-described feature. For example, a material with a sufficiently high transmittance for light of the wavelength $\lambda_1$ and with a very low transmittance for light of the wavelength $\lambda_2$ or a dielectric multilayer film is evaporated on a quartz plate, which keeps high transmittance over so wide a wavelength range as to cover the visible region and the ultraviolet region, upon the quartz plate being covered with an annular-shaped mask for making the $R_1$ region. On the other hand, the $R_2$ region is processed, in the similar manner, by evaporation of a material with a sufficiently high transmittance for light of the wavelength $\lambda_2$ and with a very low transmittance for light of the wavelength $\lambda_1$ or a dielectric multilayer film on the same quartz plate. The materials or the dielectric multilayer films have to be appropriately selected in accordance with the wavelength bands for use.

In addition, FIG. 6A schematically shows image patterns (intensity distributions) on the specimen surface 4 formed with the light of the wavelength $\lambda_1$ and the light of the wavelength $\lambda_2$, respectively. Here, a region 5 represents an image pattern by the pump light of the wavelength $\lambda_1$, and a region 6 represents an image pattern by the wavelength $\lambda_2$, which pattern shows a center drop due to the intervention of the aperture 2. According to the principle applied to the present invention, as discussed above, fluorescence is repressed in a portion where the light of the wavelength $\lambda_1$ and the light of the wavelength $\lambda_2$ overlap. In reference to the drawing, the fluorescence region is limited to a region 7 (shown with hatching). As is apparently understood from the drawing, fluorescence is emitted only from a region smaller than the region irradiated with the wavelength $\lambda_1$, Therefore, spatial resolution of the microscope is improved overcoming the diffraction limit, which depends on the wavelength in use.

Figure 7:
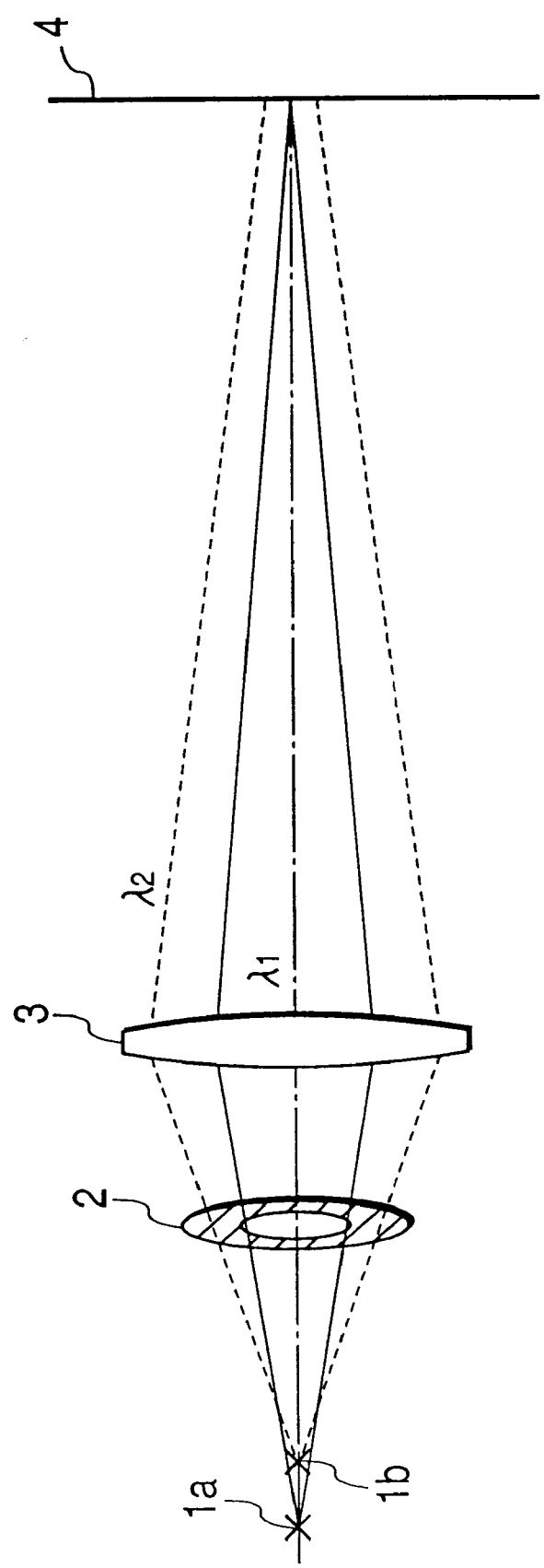
FIG. 7 shows another example of the basic configuration of the optical system shown in FIG. 6A.

According to the first embodiment, the configuration of the optical system shown in FIG. 6A may be modified, for example, as shown in FIG. 7. According to the configuration of FIG. 7, the light of the wavelength $\lambda_1$ and the light of the wavelength $\lambda_2$ are emitted from different light sources 1a and 1b, respectively, which are shifted from each other on the same optical axis. In this case, also, the light of the wavelengths $\lambda_1$ and $\lambda_2$ is incident on the aperture 2 with annular-zonal structure. The light transmitted through the aperture 2 is led to the specimen surface 4 through an optical system 3 having a single in-focus position (image characteristics) for both of the wavelength band that includes $\lambda_1$ and the wavelength band that includes $\lambda_2$. The specimen is mounted on a stage (not shown) which is movable in such a manner that the specimen can be scanned two-dimensionally on an image surface of the optical system 3 and in a direction of the optical axis, as in the configuration of FIG. 6. Similarly, the aperture 2 has the same structure as that shown in FIG. 6. According to the configuration of the optical system shown in FIG. 7, however, the light of the wavelength $\lambda_2$ is incident on the specimen surface 4 in a defocused condition due to the positional shift between the light sources 1a and 1b along the optical axis. Consequently, image patterns (intensity distributions) similar to those shown in FIG. 6A are formed on the specimen surface 4, on condition that the optical system 3 has a single in-focus position (image characteristics) for both the wavelength bands that include $\lambda_1$ and $\lambda_2$, respectively. According to the state-of-the-art lens design techniques, such an optical system is feasible as a combination of at least two lenses. Alternatively, the optical system may be constructed of a reflecting optical system, which is free from chromatic aberration in principle.

Figure 8:
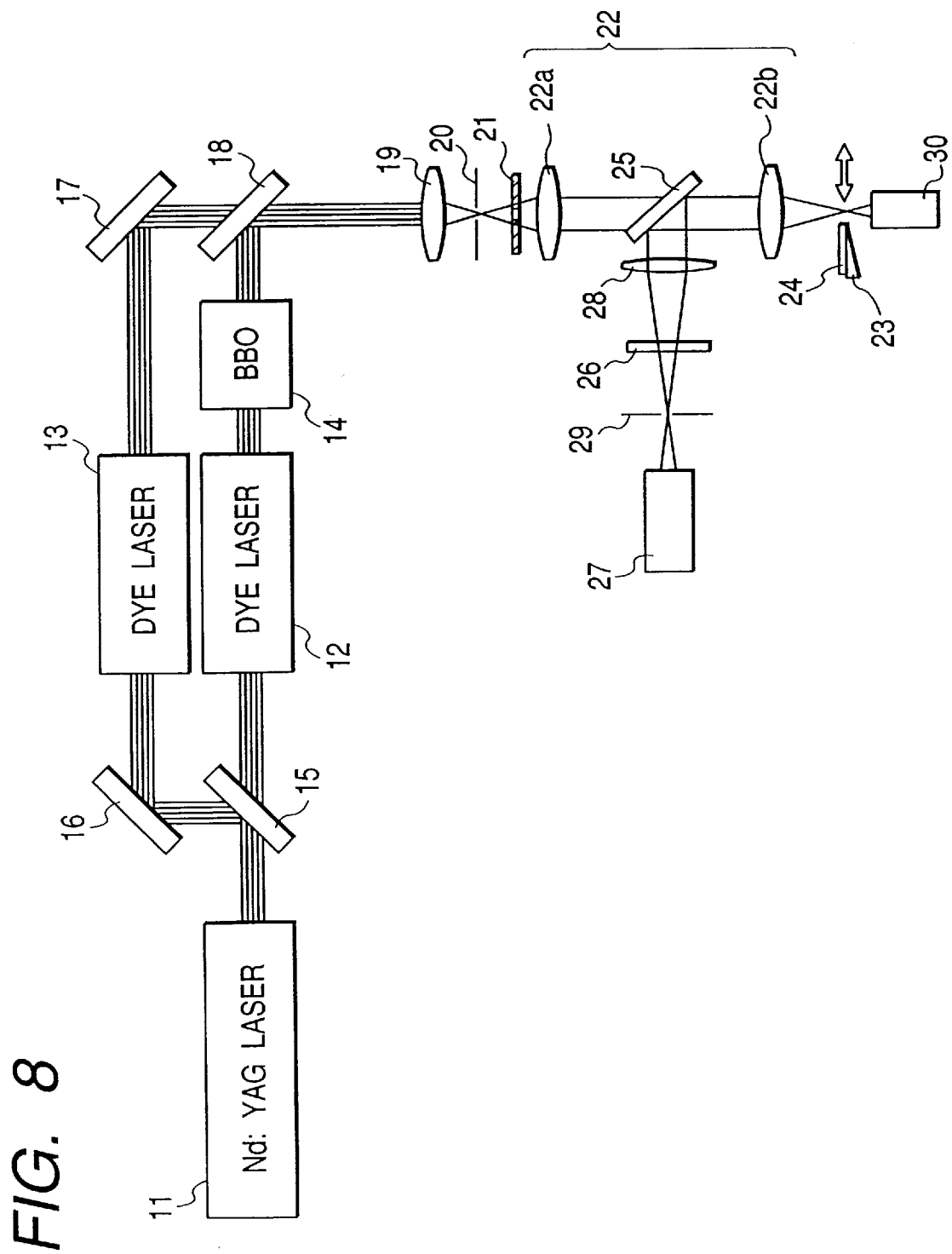
FIG. 8 shows system configuration of a scanning fluorescence microscope used in the method according to the first embodiment.

Next, in reference to FIG. 8, description is made of a specific system configuration of a scanning fluorescence microscope used for effecting the method of the first embodiment. According to the first embodiment, a Nd:YAG laser and dye lasers 12, 13 are adopted to form a light source device of the microscope system, to conform to the use of ε-adenosine as the fluorescence probe molecules. A first dye laser system is composed of the dye laser 12 and a second-harmonic oscillator 14, which is a BBO crystal. The dye laser 12, in which coumarin is used as a medium, generate light of a wavelength band 400–600 nm, upon the third harmonic (355 nm) from the Nd:YAG laser 11 being provided as exciting light. The second-harmonic oscillator converts the light of the wavelength band 400–600 nm into light of a wavelength band 200–300 nm, by which ε-adenosine can be excited from the ground state $S_0$ to $S_1$ state.

A beam of the third harmonic from the Nd:YAG laser 11 is split into two via a half mirror 15 so as to be the exciting light for the dye laser 13 also, which forms a second dye laser system. In the dye laser 13 also, coumarin is used as a medium, to generate light of the wavelength band 400–600 nm. Since this wavelength band includes a resonance wavelength to excite six-membered ring molecules from $S_1$ state to $S_2$ state (H. Kandori, et al., "Picosecond Transient Absorption of Aqueous Tryptophan", Journal of Physical Chemistry, Vol. 97, No. 38, 1993, pp. 9664–9667), ε-adenosine, which contains six-membered ring, can be excited from $S_1$ state to $S_2$ state. Additionally, in the path of a light beam in which the dye laser 13 is disposed, two mirrors 16 and 17 are arranged.

These generated beams of two colors are aligned to a same optical axis through a dichroic mirror 18. The composite light with two color components is condensed by a first focusing lens 19, which conforms to these two wavelength bands, to be incident on an aperture 21 having an annular-zonal structure. The configuration of the aperture 21 is similar to the aperture 2 shown in FIG. 6B. If the first focusing lens 19 is made achromatic with respect to these two wavelength bands, it is preferred to dispose a pinhole 20, as a spatial filter, in the in-focus position of the first focusing lens 19 for the purpose of reducing laser noise caused by undesirable diffraction or scattering.

The light beam color-separated by the aperture 21 is focused on a biological specimen 24, which is mounted on a stage 23, via a second focusing lens 22, which also conforms to the two wavelength bands. The second focusing lens 22 comprises an imaging lens 22a and an objective lens 22b. The stage 23 is made movable in the directions of the arrowheads shown in the drawing for scanning operation. Fluorescence (of wavelength $\lambda_3$) emitted by ε-adenosine in the biological specimen is reflected by a dichroic mirror 25, which is disposed between the imaging lens 22a and the objective lens 22b to transmit the wavelengths $\lambda_1$ and $\lambda_2$ and to reflect the wavelength $\lambda_3$, and then is detected by a photomultiplier 27 via a bandpass filter 26, which selectively transmits fluorescence. In addition, a third focusing lens 28 is disposed between the dichroic mirror 25 and the bandpass filter 26, and a pinhole 29 is disposed at an in-focus position of the third focusing lens 28, so that of fluorescence of the wavelength $\lambda_3$, only a portion that passes through the pinhole 29 is detected by the photomultiplier 27.

Since the scanning fluorescence microscope system used in the method of the first embodiment is configured as described above, the so-called confocal observation is possible with a resolution in the depth direction (direction of optical axis) also, and thus three-dimensional observation is possible. Also, upon an appropriate setting of the diameter of the pinhole 29 for detection of more effective signals, improvement of S/N ratio is achieved. In addition, in the microscope system, a photomultiplier 30 is disposed behind the stage 23, to facilitate the scanning operation over the stage 23.

To form the image patterns (intensity distributions) shown in FIG. 6A, the second focusing lens 22 may be constructed to have different in-focus positions for respective wavelengths, as in the configuration shown in FIG. 6A. Alternatively, the second focusing lens 22 may be configured to condense different wavelengths at an identical position (i.e. achromatic), while the first focusing lens 19 involves chromatic aberration with different in-focus positions for different wavelengths, as in the configuration shown in FIG. 7. In the latter configuration, however, the spatial filter 20 cannot be disposed because the first focusing lens 19 has different in-focus positions for the laser beams of different wavelengths.

According to the first embodiment, the Nd:YAG laser 11 to emit relatively long pulse about 7 nsec is used. Since ε-adenosine as a fluorescence probe has a much longer fluorescence lifetime about 20 nsec, use of such a Nd:YAG laser raises no problem. In addition, according to the first embodiment, a titan:sapphire laser or a semiconductor laser for CW (continuous wave oscillation) may be used as a light source device, instead of the system including the Nd:YAG laser 11 and the dye lasers 12 and 13. Alternatively, an optical parametric oscillator (OPO) laser system with variable wavelength, which recently becomes popular, is applicable. A laser system that is constructed based on a titan:sapphire laser or a Nd:YAG laser and is mode-locked to a short pulse less than 1 nsec is also applicable, as a matter of course.

The aperture 21 having the annular-zonal structure is employed for the purpose of spatially overlapping the light beams of two wavelengths with each other on the specimen. Basically, it may assume any form if it can serve to form spatially separate optical pupils differing with wavelengths. For example, a surface of the second focusing lens 22 may be coated with the materials having wavelength dependent transmittances or with the dielectric multilayered films as applied to the aperture 2 shown in FIG. 6B, to substitute the aperture 21.

Here, the fluorescence repression ratio ($F_1/F_2$) in the case of the first embodiment where ε-adenosine is used as fluorescence probe molecules is calculated in accordance with Equation (10). An absorption cross section $\sigma_{12}$ where a six-membered ring is excited from $s_1$ state to $S_2$ state is as much as $10^{-17}$ cm$^2$. (H. Kandori, et al., J. Phys. Chem. 97, 1993, 9664–9667). If the dye laser 13 emits a pulse of the fluorescence repression band (the wavelength band 400–600 including $\lambda_2$) with the photon flux $5\times10^{25}$ photons/sec/cm$^2$ for a pulse width 7 nsec, the value of the fluorescence repression ratio is 0.03. This means that the fluorescence intensity of the region irradiated with the wavelength $\lambda_2$ is repressed to 3 percent of that of the region without irradiation with $\lambda_2$. The above-supposed value of the photon flux corresponds to 25 MW/cm$^2$, if converted into the laser intensity. At present, a laser scanning fluorescence microscope utilizing the non-resonance two-photon absorption process is realized for practical use. This microscope, however, has the laser intensity that reaches several TW/cm$^2$ (K. Konig, et al. "Cellular response to near-infrared femtosecond laser pulses in two-photon microscopes", Optics Letters, Vol. 22, No. 2, Jan. 15, 1997, pp .135–136). The laser intensity according to the first embodiment is smaller than this value by a factor of 10,000 and thus one can understand that the method of the present embodiment is much less injurious for a specimen.

Figure 9:
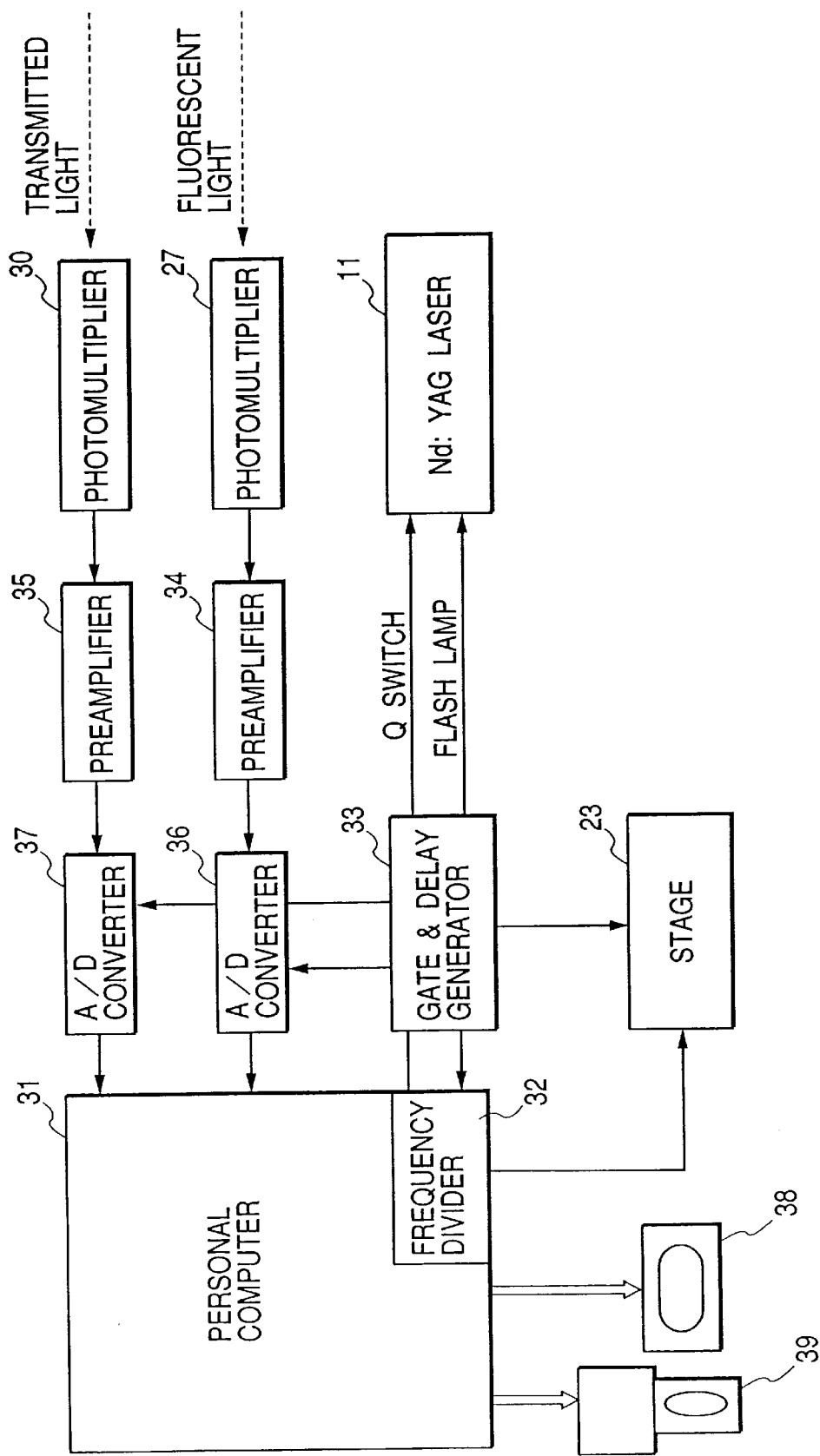
FIG. 9 is a block diagram that illustrates signal processing of the microscope system shown in FIG. 8.

The electric system shown in the diagram of FIG. 9 is applied to the microscope system shown in FIG. 8. The photomultiplier 30 monitors the light from each laser source, whereas the photomultiplier 27 monitors fluorescence from the specimen 24. An output signal from the photomultiplier 27 forms data corresponding to one pixel of a fluorescence image, while an output signal from the photomultiplier 30 represents an amount of light transmitted through the specimen 24 per shot of the laser light as the illumination light.

The entire microscope system is controlled by a personal computer 31. The personal computer 31 takes therein the signals from the photomultipliers 27 and 30, to control oscillation of the Nd:YAG laser 11 and the drive of the stage 23 on which the specimen is mounted. Every timing of the system is referenced on a clock in the personal computer 31. The clock is divided by a frequency divider 32 into a frequency at which laser oscillation is possible. The clock signal divided there is processed by a gate and delay generator 33 for delay and re-shaping of the waveform, so as to be a Q switch signal and a flash lamp signal for control of the Nd:YAG laser 11. The output signals from the photomultipliers 27 and 30 are current/voltage transformed by preamplifiers 34 and 35 and then are stored in a frame memory of the personal computer 31 as numerical data via A/D converters 36 and 37.

The timing of A/D conversion of the output signal from the photomultipliers 27 and 30 and of storage of the resulted data into the personal computer 31 is controlled by the output signals from the gate and delay generator 33, to be fully synchronized with the laser light emission, as shown in FIGS. 1–5. The stage 23 also is controlled by the personal computer 31, so that two-dimensional scanning is performed as synchronized with the laser light emission and the data storage. The image data generated through the above-mentioned procedure is output to a CRT 38 or a video printer 39.

Although the above descriptions are made based on the case where ϵ-adenosine is used as fluorescence probe molecules, another materials may be used as fluorescence probe molecules of the first embodiment. For example, molecules of each following material contain six-membered rings or double bonds, and have an extremely long fluorescence lifetime and a large fluorescence yield, so as to be preferably applicable to the super-resolution microscopy utilizing the double-resonance absorption process.

4-Fluoro-7-sulfamoylbenzofurazan:3,6-Bis (dimethylamino)-10-dodecylacridinium bromide:4-Benzylamino-7-nitrobenzofurazan:4-Azidofluorescein diacetate,5,6-Dimethoxy-2-(4-hydrazinocarbonylphenyl) benzothiazole:3-Bromomethyl,6,7-dimethoxy-1-methyl-1, 2-dihydroquinoxaline-2-one:4-Bromoethyl-7-methoxycoumarin:N-[4-(6-Dimethylamino-2-benzofurany] maleimide: 1,2-Diamino-4,5-dimethoxybenzene, dihydrochloride:2,2'-Dihydroxy-6,6'-dinaphthyl disulfide:3-Chlorocarbonyl-6,7-dimethoxy-1-methyl-2(1H)-quinoxalinone:2-2'-Dithiobis(1-aminoaphthalene), Fluorescein-4-isothiocyanate:4-Amino-3-penten-2-one:4-(4-Methoxybenzylamino)-7-nitrobenzofurazan:N-[4-(5,6-Methylenedioxy-2-benzofuranyl)]maleimide:1,2-Diamino-4,5-methylenedioxybenzene:N-(9-Acridinyl)maleimide:4-Fluoro-7-nitrobenzofurazan,4-Chloro-7-nitrobenzofurazan: (S)-(−)-1-(2,3-Napthalenedicarboximidyl fluoride:2-(5-Chlorocarbonyl-2-oxazolyl)-5,6-methylenedioxybenzofuran:4-Chloro-7-sulfobenzofurazan, ammonium salt:4-Fluoro-7-sulfobenzofurazan, ammonium salt:Sulforthodamine 101 acid chloride:4-[4 (Dimethylamino)phenylazo]phenylisothiocyanate:3,5-Dinitrobenzoyl chloride:5-(4-Dimethylaminophenyl)-2,4-pentadienal:1,3-Diphenyl-2-thiobarbituric acid:O-(4-Nitrobenzyl)-N,N'-diisopropylisourea:O-(4-Nitrobenzyl) hydroxylamine,hydrochloride: N,N,N'-Triethyl-N'-[N-(N-succinimidyloxycarbonyl)pentyl]-9-cyanopyronine chloride: N,N,N'-Triethyl-N'-{5-[N"-(2-maleimidoethyl) piperazinocarbonyl]pentyl}9-cyanopyronine chloride:2,4'-Dibromoacetophenone:N-Succinimidyl-4-nitrophenylacetate:

O,O'-Bis(2-aminophenyl)ethyleneglycol-N,N,N',N'-tetraacetic acid, tetraapotassium,hydrate:O,O'-Bis(2-aminophenyl) ethyleneglycol-N,N,N',N'-tetraacetic acid, tetraacetoxymethyl ester:O,O'-Bis(2-amino-5-fluorophenoxy) ethyleneglycol-N,N,N',N'-tetraacetic acid, tetraapotassium,hydrate:O,O'-Bis(2-amino-5-fluorophenoxy)ethyleneglycol-N,N,N',N'-tetraacetic acid, tetraacetoxymethyl ester:N,N,N',N'-Tetrakis (2-pyridylemethyl) ethylenediamine:1-[2-amino-5-(2,7-dichloro-6-hydroxy-3-oxy-9-xantheny)]-2-(2-Amino-5-methylphenoxy)ethane-N,N,N',N'-tetraacetic acid:1-[2-Amino-5-(2,7-dichloro-6-hydroxy-3-oxy-9-xantheny)]-2-(2-amino-5-methylphenoxy) ethane-N,N,N',N'-tetraacetic acid,pentaacetoxymethyl estar:1-[6-Amino-2-(5-carboxy-2-oxazolyl)-5-benzofuranyloxy]-2-(2-amino-5-methylphenoxy)ethane-N,N,N',N'-tetraacetic acid, pentapotassium salt:1-[6-Amino-2-(5-carboxy-2-oxazolyl)-5-benzofuranyloxy]-2-(2-amino-5-methylphenoxy)ethane-N,N,N',N'-tetraacetic acid, pentaacetoxymethyl ester:1-[6-Amino-5-(6-carboxy-2-indolyl) phenoxy]-2-(2-amino-5-methylphenoxy)ethane-N,N,N',N'-tetraacetic acid, pentapotassium salt:1-[6-Amino-5-(6-carboxy-2-indolyl) phenoxy]-2-(2-amino-5-methylphenoxy)ethane-N,N,N',N'-tetraacetic acid, pentaacetoxymethyl ester:8-Amino-2-[2-amino-5-methylphenoxy)methyl]-6-methoxyquinoline-N, N,N',N'-tetraacetic,tetrapotassium salt:8-Amino-2-[(2-amino-5-methylphenoxy)methyl]-6-methoxyquinoline-N, N,N',N'-tetraacetic, tetraacetoxymethyl ester:1-[(2-Amino-5-(3-dimethylamino-6-dimethylammonio-9-xanthenyl]-2-(2-amino-5-methylphenoxy)ethane-N,N,N',N'-tetraacetic acid, chloride:1-[(2-Amino-5-(3-dimethylamino-6-dimethylammonio-9-xanthenyl]-2-(2-amino-5-methylphenoxy)ethane-N,N,N',N'-tetraacetic acid, tetraacetoxymethyl ester,chloride:2'.7'-Bis(carboxyethyl)-4 or 5-carboxyfluoreescein:

3'-O-Acetyl-2',7'-bis(carboxyethyl)-4 or 5 carboxyfluorescien, diacetoxymethyl ester:8-Amino-2-(trans-2-aminostyryl)-6-methoxyquinoline-N,N,N',N'-tetraacetic acid, tetrapotassium salt:8-Amino-2-(trans-2-aminostyryl)-6-methoxyquinoline-N,N,N',N'-tetraacetic acid, tetraacetoxymethyl ester:4,4'-Bis[{6-[N,N-bis(2-hydroxyethyl)amino]-4-phenylamino-1,3,5-triazin-2-yl}amino]-2,2'-stilbenedisulfonic acid, disodium salt:4.4'-Bis[{6-[N,N-diethylamino]-4-phenylamino-1,3,5-triazin-2-yl}amino]-2,2'-stilbenedisulfonic acid,disodium salt:4,4'-Bis[(6-methoxy-4-phenylamino-1,3,5-triazin-2-yl)amino]-2,2'-stilbenedisulfonic acid,disodium salt:1,3-Bis(1-pyrenyl)propane, 1-(4-Trimethylammoniumphenyl)-6-phenyl-1,3,5-hexatriene iodide: N-[3-(1,5-Disulfonaphtyl)]-N'-[4-(2,2,6,6-tetramethylpiperidine-N-oxide)thiouurea, disodium salt:N-Ethoxycarbonylmethyl-6-methoxyquinolinium promide:6-Methoxy-N-(3-sulfopropyl) quinolinium,monohydrate:5- or -6-(N-Succinimidyloxycarbonyl)-3',6'-diacetylfluorescein:5- or -6-(N-Succiniumidyloxycarbonyl)-4',5'-diamethyl-3',6'-O,O'-diacetylfluorescein:5- or -6-(N-Succiniumidyloxycarbonyl)-4',5'-dichloro-3',6'-O,O'-diacetylfluorescein:

3,6-bis-dimethylaminoacridine:9-aminoacridine:9-(4-diethylamino-methylfbutylamino)-3-chloro-7-methoxyacridine:1-anilinonaphthalene-8-sulfonate:N-methyl-2-anilinonaphthalene-6-sulfonate:2-p-toluidinylnaphthalene-6-sulfonate:12(9-anthroyloxy)stearic acid: teramethyldiaminodiphenylketoimine hydrochloride:7-chloro-4-dimethylamino-1,4,4a,5,5a,6,11,12a-octahydro-3,6,10,12,12a-pentahydroxy:cyanine dyes:1,1'-dihexyl-2,2'-oxacarbocyanine:3,3'-dipropylthiadicarbocyanine:5-[(3-sulfopropyl-2(3H)-benzoxazolylidene)-2-butenylidene]-1,3-dibutyl-2-thiobarbituric acid:5-dimethylaminonaphthalene-1-sulfonamide:dansylamino-ethyltriphosphate:1-(5-dimethylaminonaphthalene-1-sulfonamide)-3-N,N,-dimethyaminopropane:1-(5-dimethylaminonaphthalene-1-sulfonamido)-propane-3-trimethlammonium: (N-dansyl)-aminoalkyl-β-D-galactopyranoside: ε-dansyl-L-lysine:dansylphosphaidyl-ethanolamine:1,6-diphenyl-1,3,5-hexatriene: 2',4',5',7'-tetrabromofluorescein:1,N6-ethennoadenosine:2,7-diamino-9-phenylphenanthrium-10-ethyl-bromide:9-(o-carboxyphenyl)-6-hydroxy-3H-xanthen-3-one:

7-amino-3-(β-D-ribrofuranosyl)pyrazolo (4,3-d) pyrimidine:4-benzoylamido-4'-aminostilbene-2-2'-disulfonate:1-acyl-2-[N-(4-nitrobenzo-2-oxa-1,3-diazolyl) aminocaproyl]phosphatridylcholine: β-naphthyltriphosphate:oxonol dye:bis [3-phenyl-5-oxoisoxazol-4-yl]pentamethineoxonol:bis[1,3-dibutylbarbituric-acid(5)]pentamethineoxonol:α(9,11,13,15-cis.trans,trans,cis)octadecatetraenoic acid:β(9,11,13,15-all,trans)octadecateraenoic acid:perylene:N-phenyl-1-napthylamine:pyrene: 2,3-dimethyl-3,7-diamino-5-phenylphenazium: 4-phenylspro[furan-2(3H),1'-futalan]-3,3'-dione:o-phthalic dicarboxaldehyde:1-dimethylaminonaphthalene-5-sulfonyl chloride:flurorescien isothiocyanate:7-chloro-4-nitrobenzo-2-oxal,3-diazole:N-dansyl aziridine:5-(iodoacetoamidoethyl)amino-naphthalene-1-sulfonate:5-iodoacetamido fluorescein:N-(1-anilinonaphthyl-4)maleimide:N-(7-dimethylamino-4-methylcoumarynul)maleimide:N-(3-pyrene) maleimide:eosin-5-iodoacetamide:fluorescein mercury-acetate:2-[4'(2"-iodoacetamido)pheyl]aminonaphthalene-6-sulfonic acid:

Of the above-listed materials, many fluorescence probes such as o-phthalaldehyde (o-phthalic dicarboxaldehyde) maintain stable and strong fluorescence intensity as they are in a solution of pH 6–11.5 to allow a pixel to be formed with a stable signal intensity, and thus a good microscopic image can be expected. Therefore, the advantage of the present invention can be fully exploited to obtain an image with high quality if the dyed specimen is bathed in a buffer solution of pH 6–11.5.

Second Embodiment

Figure 10:
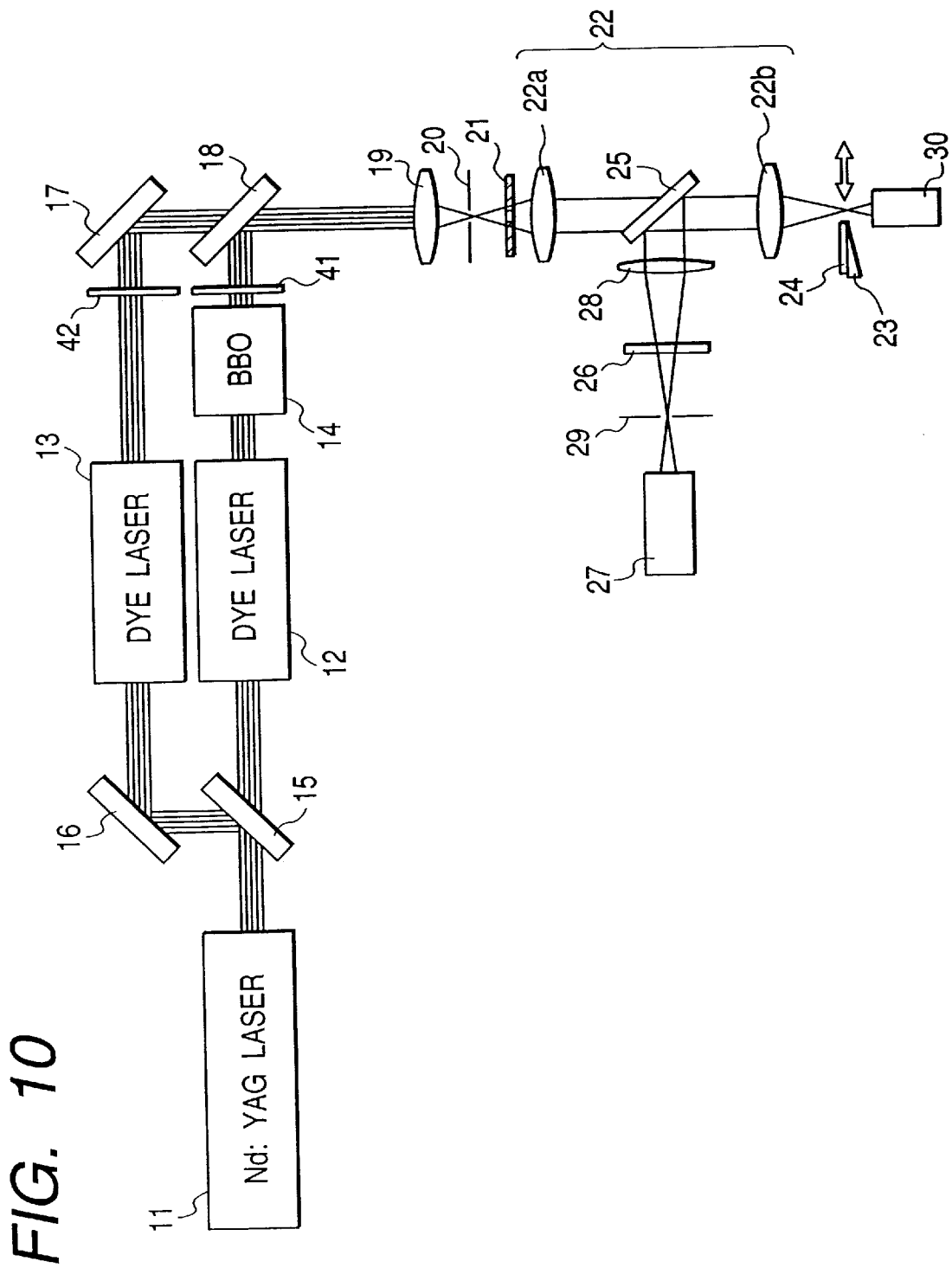
FIG. 10 shows system configuration of a scanning fluorescence microscope used in the method according to the second embodiment.
Figure 11:
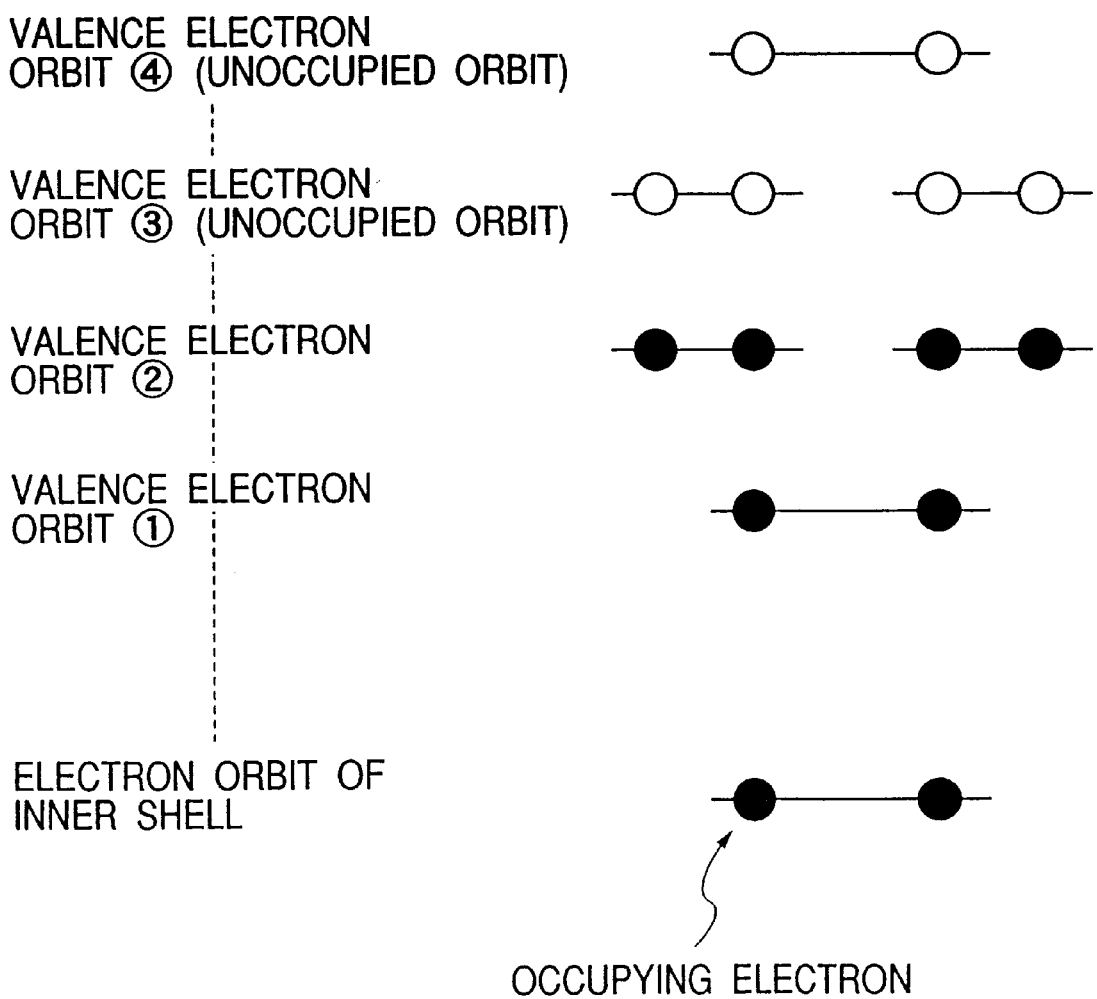
FIG. 11 schematically shows an electronic structure of a molecule.
Figure 12:
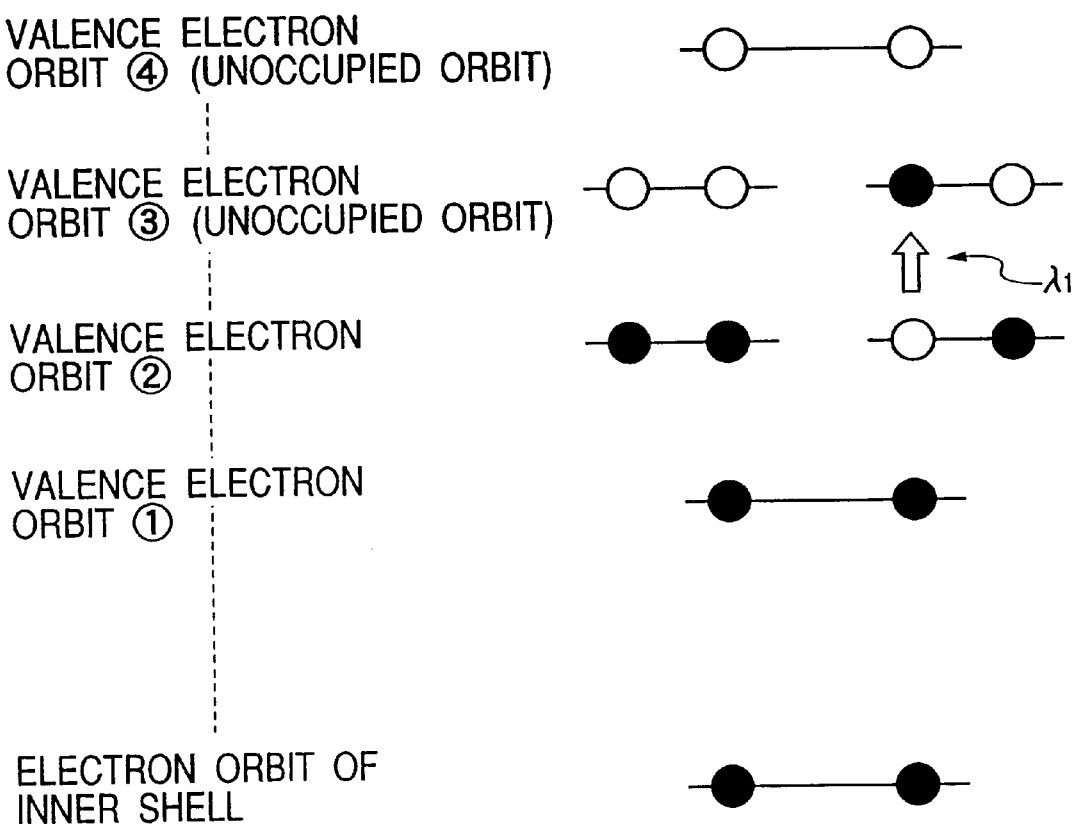
FIG. 12 schematically shows an electronic structure where the molecule shown in FIG. 11 is excited by light of a wavelength $\lambda_1$ to cause transition from $S_0$ state to $S_1$ state.
Figure 13:
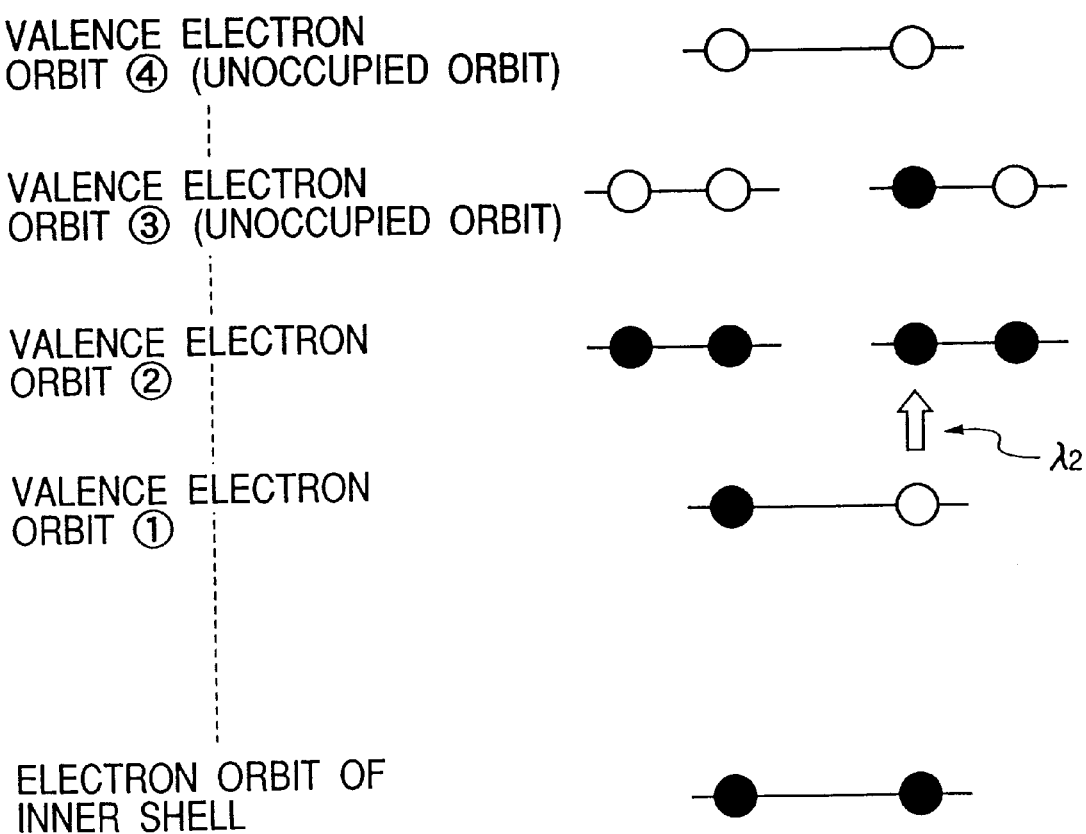
FIG. 13 schematically shows an electronic structure where the molecule shown in FIG. 12 is excited by light of a wavelength $\lambda_2$ to cause transition from $S_1$ state to $S_2$ state.
Figure 14:
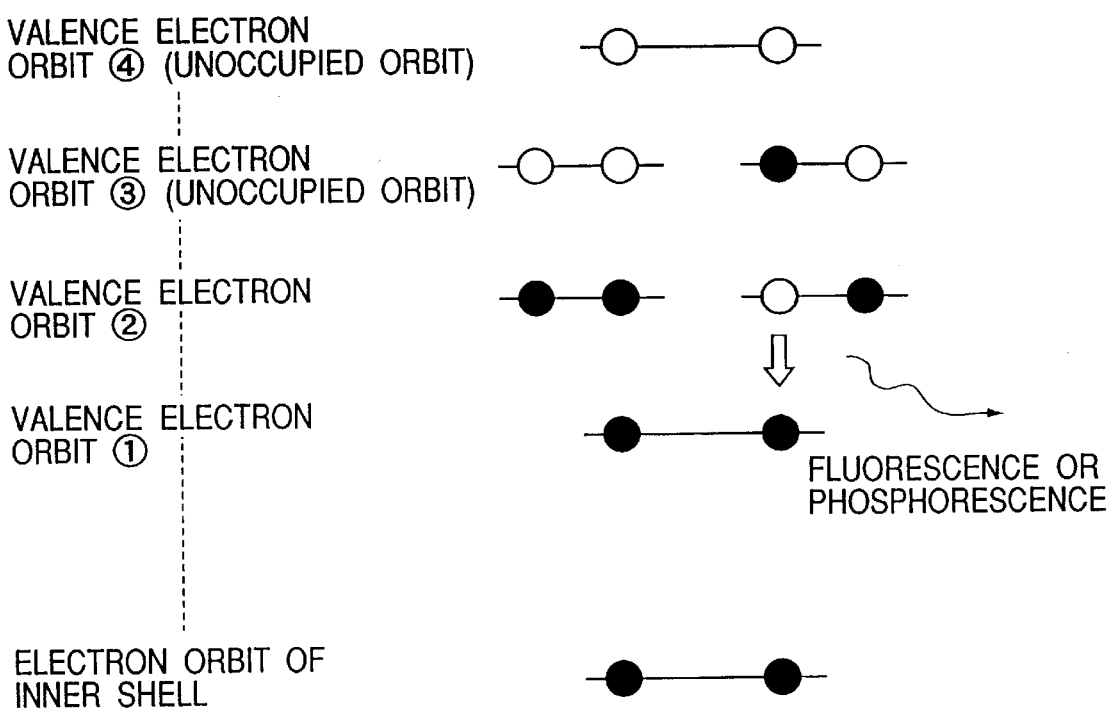
FIG. 14 schematically shows decay process of the molecule from the $S_2$ state shown in FIG. 13, where the process is accompanied by luminescence.
Figure 15:
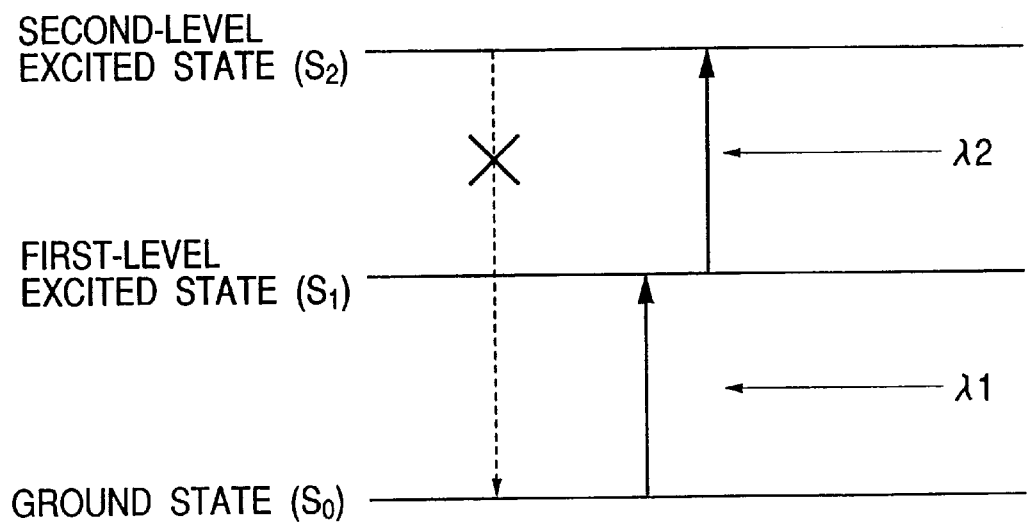
FIG. 15 schematically illustrates the case where decay process of a molecule from $S_2$ state, which state is a result of the double-resonance absorption process, is not accompanied by fluorescence or phosphorescence.
Figure 16:
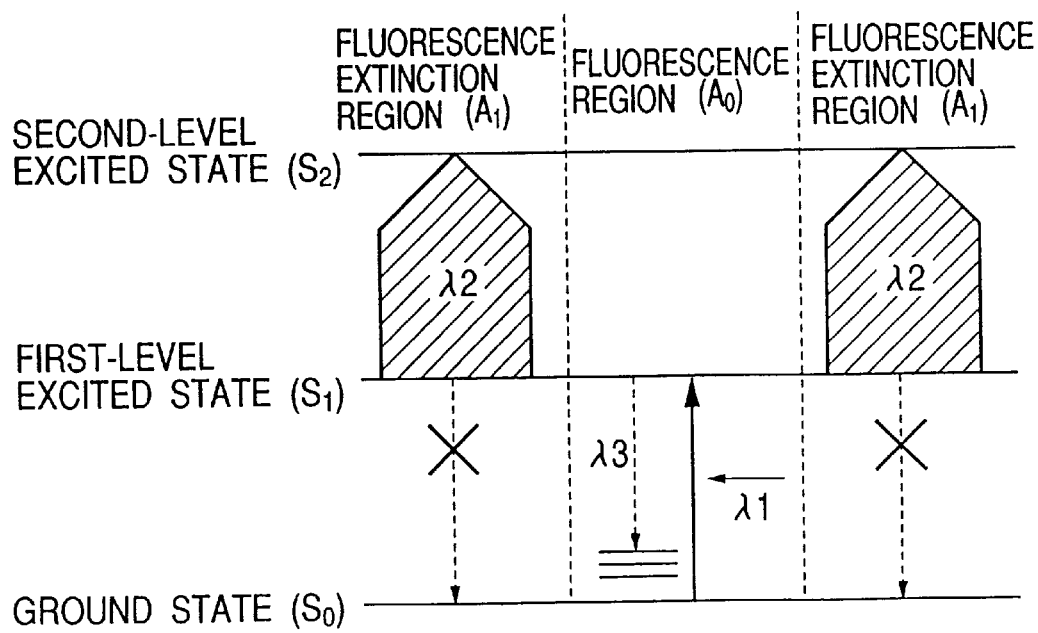
FIG. 16 schematically illustrates the principle of super-resolution microscopy, where molecules having small luminance yield from $S_2$ state are used.

The method according to the second embodiment is similar to that of the first embodiment, but is different in that the observation is performed via a scanning microscope shown in FIG. 10. In the scanning microscope shown in FIG. 10, in addition to the configuration of the microscope used in the first embodiment, two polarizers 41 and 42 are disposed on the exit sides of the second-harmonic oscillator 14 and the dye laser 13, respectively. Such an arrangement of the polarizers 41 and 42 allows the polarization planes of the laser light waves that are oscillated by the two dye lasers 12 and 13, respectively, to be controlled independent of each other. The relation between the polarization planes of two light waves and the direction of orientation of a molecule strongly affects the double-resonance absorption process. The double-resonance absorption process depends on an angular relationship between the respective polarization planes of the light waves and the orientation of the molecules, and a strong absorption of the probe beam can be observed in the particular relationship. Thus, an observer could obtain information on distribution of spatial orientation of the specimen 24 by observing change of degree of fluorescence extinction.

To be specific, the laser beams of two wavelengths are transmitted through the polarizers 41 and 42, respectively, so that their polarization planes are preset before the irradiation of the specimen 24. Only when a certain condition is satisfied between the polarization conditions of the laser beams and the direction of orientaion of a molecule, the double-resonance absorption process intensely occurs and consequently fluorescence extinguishes from the molecule oriented in this direction. Analysis of the spatial orientation of the specimen 24 thus is possible upon observation of the amount of decrease of fluorescence.

Therefore, according to the method of the second embodiment, analysis of the spatial orientation of tissues of the specimen is possible, in addition to that super-resolution is attained. Also, the microscope used in the second embodiment may be modified so that the polarization planes of two light waves having different wavelengths are controllable correlative to each other.

As discussed above, according to the method of microscopic observation of the present invention, a microscopic image with high spatial resolution is obtained by irradiating a dyed specimen with a plurality of light beams of different wavelengths.

What is claimed is:

1. A method of microscopic observation, comprising:

dying a specimen with molecules each having at least three quantum states inclusive of a ground state; and observing the specimen through a microscope, said microscope comprising:

a light source device constructed and arranged to emit light of a wavelength $\lambda_1$ that excites the molecules from a ground state to a first-level excited state and light of a wavelength $\lambda_2$ that excites the molecules from the first-level excited sate to a second-level excited state, said second-level excited state being higher in energy than said first-level, a focusing optical system for focusing the light of the wavelength $\lambda_1$ and the light of the wavelength $\lambda_2$ on the specimen, a photodetector for detecting luminescence which occurs according as the molecules, with which the specimen is dyed, decay to return to the ground state; and an irradiation overlapping assembly constructed and arranged to overlap a region irradiated with the light of the wavelength $\lambda_1$ with a region irradiated with the light of the wavelength $\lambda_2$ so that a region in which the luminescence accompanying a decay of the molecules from the first-level excited state to the ground state is limited by said irradiation overlapping assembly through which the specimen is irradiated with the light of the wavelength $\lambda_1$ and the light of the wavelength $\lambda_2$, wherein the molecules with which the specimen is dyed are used as fluorescence probe molecules and have such a property that a relaxation process with heat emission is predominant over a relaxation process with fluorescence emission in a transition of decay from a higher-level energy state other than the first-level excited state to the ground state, and wherein the wavelength $\lambda_2$ is different from a wavelength of the luminescence emitted from the specimen.

2. A method of microscopic observation according to claim 1, wherein said microscope is constructed so that polarization conditions of the light of the wavelength $\lambda_1$ and the light of the wavelength $\lambda_2$ are controllable independent of one another.

3. A method of microscopic observation according to claim 1, wherein said microscope is constructed so that polarization conditions of the light of the wavelength $\lambda_1$ and the light of the wavelength $\lambda_2$ are controllable correlative to one another.

4. A method of microscopic observation according to any one of claims 1, 2 or 3, wherein a time duration of irradiation with the wavelength $\lambda_1$ and the wavelength $\lambda_2$ is one tenth of a fluorescence lifetime of the molecules with which the specimen is dyed.

5. A method of microscopic observation according to claim 1, wherein each of the molecules with which the specimen is dyed forms a double bond.

6. A method of microscopic observation according to claim 1, wherein each of the molecules with which the specimen is dyed contains at least one six-membered ring as a chemical base.

7. A method of microscopic observation according to claim 1, wherein a time duration of irradiation with the wavelength $\lambda_1$ and the wavelength $\lambda_2$ is shorter than a lifetime of the molecules with which the specimen is dyed.

8. A method of microscopic observation according to claim 1, wherein the specimen is irradiated with the light of the wavelength $\lambda_1$ and the light of the wavelength $\lambda_2$ simultaneously.

9. A method of microscopic observation according to claim 1, wherein irradiation with the light of the wavelength $\lambda_1$ is completed before irradiation with the light of the wavelength $\lambda_2$ is commenced.

10. A method of microscopic observation according to claim 1, wherein time duration of irradiation with the light of the wavelength $\lambda_2$ is longer than that with the light of the wavelength $\lambda_1$.

11. A method of microscopic observation according to claim 1, wherein detection of fluorescence is performed after irradiation with the light of the wavelength $\lambda_1$ and with the light of the wavelength $\lambda_2$ is completed.

12. A method of microscopic observation according to claim 1, wherein the molecules with which the specimen is dyed has a fluorescence lifetime longer than 1 nsec.

13. A method of microscopic observation according to claim 1, further comprising a step of bathing the specimen dyed with the molecules in a solution of pH 6–11.5 before the step of observing the specimen through said microscope.

14. An optical apparatus comprising:
 a light source device that illuminates a specimen dyed with fluorescence probe molecules;
 a focusing optical system that focuses light from said light source device on the specimen;
 an optical member disposed between said light source device and said focusing optical system; and
 a detecting optical system that detects light from the specimen;
 wherein said light source device emits light of a wavelength $\lambda_1$, which excites the fluorescence probe molecules from a ground state to a first-level excited state, and light of a wavelength $\lambda_2$, which excites the fluorescence probe molecules from the first-level excited state to a second-level excited state, said second level excited state being higher in energy than the first-level excited state, and said light of wavelength $\lambda_2$ is different from fluorescence emitted from the specimen in wavelength,
 wherein said optical member has such a transmission pattern that the light of the wavelength $\lambda_1$ and the light of the wavelength $\lambda_2$ partially overlap with one another on a surface of the specimen, and
 wherein said fluorescence probe molecules have at least three quantum states inclusive of the ground state and have such a property that a relaxation process with heat emission is predominant over a relaxation process with fluorescence emission in a transition of decay from a higher-level energy excited state other than the first-level excited state to the ground state.

* * * * *